US007605235B2

(12) United States Patent
Anderson et al.

(10) Patent No.: US 7,605,235 B2
(45) Date of Patent: Oct. 20, 2009

(54) ANTI-TISSUE FACTOR ANTIBODIES AND COMPOSITIONS

(75) Inventors: G. Mark Anderson, Norristown, PA (US); Bernard Scallon, Wayne, PA (US); Michael Naso, Philadelphia, PA (US); Ann Cai, West Chester, PA (US); Cam Ngo, Philadelphia, PA (US)

(73) Assignee: Centocor, Inc., Malvern, PA (US)

( * ) Notice: Subject to any disclaimer, the term of this patent is extended or adjusted under 35 U.S.C. 154(b) by 458 days.

(21) Appl. No.: 11/010,797

(22) Filed: Dec. 13, 2004

(65) Prior Publication Data
US 2005/0220793 A1 Oct. 6, 2005

Related U.S. Application Data

(63) Continuation-in-part of application No. 10/855,664, filed on May 27, 2004.

(60) Provisional application No. 60/475,174, filed on May 30, 2003.

(51) Int. Cl.
C12P 21/08 (2006.01)
(52) U.S. Cl. .................. 530/387.9; 424/178.1
(58) Field of Classification Search .......... None
See application file for complete search history.

(56) References Cited

U.S. PATENT DOCUMENTS

| 5,223,427 | A | 6/1993 | Edgington et al. | |
|---|---|---|---|---|
| 5,589,173 | A | 12/1996 | O'Brien et al. | |
| 5,726,147 | A | 3/1998 | Ruf et al. | |
| 5,766,591 | A | 6/1998 | Brooks et al. | |
| 5,986,065 | A | 11/1999 | Wong et al. | |
| 6,001,978 | A | 12/1999 | Edgington et al. | |
| 6,036,955 | A | 3/2000 | Thorpe et al. | |
| 6,238,878 | B1 | 5/2001 | Jakobsen et al. | |
| 6,274,142 | B1 | 8/2001 | O'Brien et al. | |
| 6,342,219 | B1 * | 1/2002 | Thorpe et al. ............ | 424/145.1 |
| 6,555,319 | B2 | 4/2003 | Wong et al. | |
| 6,677,436 | B1 | 1/2004 | Sato et al. | |
| 6,703,494 | B2 | 3/2004 | Kirchhofer et al. | |
| 7,235,380 | B1 * | 6/2007 | Joliffe et al. ............. | 435/69.1 |

FOREIGN PATENT DOCUMENTS

| EP | 0833911 B1 | 6/1996 |
|---|---|---|
| EP | 1069185 A1 | 2/1999 |
| WO | WO 88/07543 A1 | 10/1988 |
| WO | WO 91/09968 A1 | 7/1991 |
| WO | WO 94/05328 A1 | 3/1994 |
| WO | WO 94/11029 A1 | 5/1994 |
| WO | WO 96/40921 A1 | 12/1996 |
| WO | WO 9640921 A1 | 12/1996 |
| WO | WO 01/70984 A2 | 9/2001 |
| WO | WO 01/24626 A1 | 12/2001 |
| WO | WO/03/018771 * | 3/2003 |
| WO | WO 03/029295 A1 | 4/2003 |
| WO | WO 03037911 A2 | 5/2003 |
| WO | WO 2004/039842 A2 | 5/2004 |
| WO | WO 2004039842 A2 | 5/2004 |
| WO | WO 2004094475 A2 | 11/2004 |

OTHER PUBLICATIONS

Rudikoff et al. Proc Natl Acad Sci USA 1982 vol. 79 p. 1979.*
MacCallum et al. J. Mol. Biol. (1996) 262, 732-745.*
Pascalis et al. The Journal of Immunology (2002) 169, 3076-3084.*
Casset et al. (2003) BBRC 307, 198-205.*
Vajdos et al. Journal of Molecular Biology. (2002) 320, 415-428.*
Chen et al. J. Mol. Bio. (1999) 293, 865-881.*
Wu et al. J. Mol. Biol. (1999) 294, 151-162.*
Holm et al. Molecular Immunology, (2007) 44, 1075-1084.*
Mueller et al. PNAS vol. 89 pp. 11832-11836, Dec. 1992.*
Reff et al. (Critical Reviews in Oncology/Hematology, vol. 40, pp. 25-35, 2001).*
Ruf, Wolfram et al, Purification, sequence and crystallization of an anti-tissue factor, Journal of Crystal Growth 122 (1992), 253-264.
Morrisey et al (1988), "Monoclonal Antibody analysis of purified and cell-associated tissue factor" Thrombosis Research 52:2.
Morrisey et al (1987) "Molecular cloning of the cDNA for tissue factor, the cellular receptor for the initiation of the coagulation protease cascade" Cell 50:129-135.
Owens et al, (1994)"The genetic engineering of monoclonal antibodies" Journal of Immunological Methods 168:149-165.
Ruf et al, (1991) "An anti-tissue factor monoclonal antibody which inhibits TF-Vlla complex is a potent anticoagulant in plasma" Thrombosis and Haemostasis 66:529-533.
Winter et al, (1993)"Humanized antibodies" Immunology Today 14:243.
Fiore, Martine et al, (1992) An Unusual Antibody that Blocks Tissue Factor/Factor Vlla Function by Inhibiting cleavage Only of Macromolecular Substrates Blood, vol. 80, No. 12, 3127-3134.
Ragni, Massimo et al, (1996) "Monoclonal Antibody Against Tissue Factor Shortens Tisue Plasminogen Activator LysisTime and Prevents Reocclusion in a Rabbit Model of Carotid Artery Thrombosis" Ciruclation vol. 93, No. 10, 1913-1918.

(Continued)

Primary Examiner—Larry R. Helms
Assistant Examiner—Meera Natarajan
(74) Attorney, Agent, or Firm—Kenneth J. Dow

(57) ABSTRACT

Isolated anti-tissue factor antibodies, immunoglobulins, cleavage products and other specified portions and variants thereof having enhanced ADCC activity, as well as anti-tissue factor antibody compositions, encoding or complementary nucleic acids, vectors, host cells, compositions, formulations, devices, transgenic animals, transgenic plants, and methods of making and using thereof. The antibodies of the invention bind human tissue factor and demonstrate enhanced ADCC activity. Accordingly, the antibodies can be used in a variety of methods for diagnosing, treating, and/or preventing diseases involving tissue factor, where enhanced ADCC activity is desirable such as cancer.

9 Claims, 19 Drawing Sheets

OTHER PUBLICATIONS

Ardissino, diego et al (2001) "Thrombogenic potential of human coronary atherosclerotic plaques" Blood vol. 98, No. 9, 2726-2729.

Presta, Leonard et al (2001) "Generation of a Humanized, High affinity Anti-Tissue Factor Antibody for Use as Novel Antithrombotic Therapeutic" Thromb Haemost 2001; 85; 379-89.

Carson, Steven et al (1987) "An Inhibitory Monoclonal Antibody Against Human Tissue Factor" Blood vol. 70, No. 2, 490-493.

Paborsky, Lisa et al (1990) "Mammalian cell transient expression of tissue factor for the production of antigen" Protein Engineering vol. 3, No. 6, 547-553.

Tanaka, H et al (1985) "Purification of Glycosylated Apoprotein of Tissue Factor Brain and Inhibition of its Procoagulant Activity by a Specific Antibody" Thrombosis Research 40:745-756.

Kirchhofer, Daniel et al, (2000) "Epitope Location on Tissue Factor Determines the Anticoagulant Potency of Monoclonal Anti-tissue Factor Antibodies," Thromb Haemost 2000, 84:1072-81.

Huang, Mingdong et al (1998) "The Mechanism of an Inhibitory Antibody on TF-initiated Blood Coagulation Revealed by the Crystal Structures of Human Tissue Factor, Fab 5G9 and TF 5G9 Complex." J. Mol. Biol. 275, 873-894.

Chen, Jiang et al, (2001) Tissue Factor—A Receptor Involved in the Control of Cellular Properties, Including Angiogenesis Thromb Haemost 2001, 86:334-345.

Rao, Chilukuri N. et al (2001) "Expression of Tissue Factor Pathway Inhibitor 2 Inversely Correlates during the Progression of Human Gilomas" Clinical Cancer Research vol. 7, 570-576.

Mechtcheriakova, Diana et al (2001) "Specificity, diversity, and convergence in VEGF and TNG—signaling events leading to tissue factor up-regulation via EGR-1 in endothelial cells." FASEB J. 2001, 15: 230-242.

Shen, Ben Quan et al (Feb. 16, 2001) "Vascular Endothelial growth Factor KDR Receptor Signaling Potentiates Tumor Necrosis Factor-induced Tissue Factor Expression in Endothelial Cells." The Journal of Biological Chemistry. vol. 276, No. 7, 5281-5286.

Hu et al, (2001) "Targeting tissue factor on tumor vascular endothelial cells and tumor cells for immunotherapy in mouse models of prostatic cancer." Department of Molecular Biophysics and Biochemistry, Yale University, vol. 98, No. 21, 12180-12185.

Nilsson et al; (2001) "Targeted Delivery of Tissue Factor to the ED-B Domain of Fibronectin, a Marker of Angiogenesis, Mediates the Infaarction of Solid tumors in Mice." Cancer Research, vol. 61, 711-716.

Hu et al, (1999) "Targeting tumor vasculature endothelial cells and tumor cells for immunotherapy of human melanoma in a mouse xenograft model." Proc. National Acad. Sci. vol. 96, pp. 8161-8166, USA.

Ran et al, (1998) "Infarction of solid Hodgkin's tumors in mice by antibody-directed targeting of tissue factor to tumor vasculature." Cancer Research, vol. 58, Issue 20, p. 4646-4653, USA.

Huang et al, (1997) "Tumor Infarction in Mice By Antibody-Directed Targeting of Tissue Factor to Tumor Vasculature." Science vol. 275, pp. 547-550.

Amirkhosravi et al, (2002), "Tissue Factor Pathway Inhibitor Reduces Experimental Lung Metastasis of B16Melano a. "Throm Haemost, vol. 87, 930-936.

Palumbo et al, (2000), Fibrinogen is an important determinant of the metastatic potential of circulating tumor cells, Blood, vol. 96 (10) 3302-3309.

Hembrough et al (2003) "Tissue Factor/Factor Vlla Inhibitors block angiogenesis and Tumor Growth Through A Nonhemostatic Mechanism," Cancer Reseach, vol. 63, pp. 2997-3000.

Bromberg et al (1995), "Tissue Factor promotes melanoma metastasis by a pthway independent of blood coagulation." Proc. Natl Acad. Sci., vol. 92, pp. 8205-8209, USA.

Bazan, J. Fernando (1990) "Structural design and molecular evolution of a cytokine receptor superfamily" Proc. Natl Acad. Sci, USA., vol. 87, pp. 6934-6938, Biochemistry.

Ruf et al, (1999), "Tissue Factor Signaling" Thrombosis and Haemostasis—82 (2) 175-182, The Scripps Research Institute, USA.

Versteeg et al, (2001) "The Pleiotropic Effects of Tissue Factor: A Possible Role for Factor Vlla-induced Intracellular Signalling?" Thromb Haemost 2001, 86: 1353-9., Schattauer GmbH. Stuttgart.

Bach et al, (1997), "Mechanism of Tissue Factor Activation on HL-60 Cells", Blood, vol. 89, No. 9, pp. 3270-3276.

Refino et al, (1999) "A Human Antibody that Binds to the y-carboxyglutamic Acid Domain of Factor IX is a Potent Antithrombotic In Vivo," Thromb. Haemost, 82: 1188-95.

Presta et al, (2001) "Generation of a Humanized, High Affinity Anti-tissue Factor Antibody for Use as a Novel Antithrombotic Therapeutic", Thromb Haemost, 85: 379-89..

Jolliffe et al, U.S. Appl. No. 10/313,392, filed Dec. 4, 2002 (pending).

Ngo, C. et. al.: "CTNO 859, A Humanized Anti-tissue Factor Monoclonal Antibody Inhibits Lung Metastasis and Tumor Growth In MDA-MB-231 Breast Cancer Xonograft Models" Pathophysiology of Haemostasis and Thrombosis, Karger, CH, vol. 33, No. Suppl 1 Sep. 2003, p. 71 XP009082975, ISSN: 1424-8832.

Ngo, Cam V. et. al: "CTNO 859, A Humanized Anti-tissue Factor Monoclonal Antibody, is a Potent Inhibitor of Breast Cancer Metastasis and Tumor Growth in Xenograft Models" International Journal of Cancer, vol. 120, No. 6, Mar. 2007, pp. 1261-1267, XP002432052, ISSN: 0020-7136.

Supplementary Partial European Search Report for EP Appln. No. EP04776131 dated May 16, 2007.

Louis M. Weiner, "An Overview of Monoclonal Antibody Therapy of Cancer," Seminars in Incology, 26(4): 41-50 (1999).

Rakesh K. Jain, "Barriers to Drug Delivery in Solid Tumors," Scientific American, 271(1): 58-65 (1994).

Robert O. Dillman, "Monoclonal Antibodies for Treating Cancer," Annals of Internal Medicine, 111: 592-603 (1989).

Fernandez, et al., "Tissue factor and angiogenesis in cancer," Current Opinion in Hematology, 9:401-406 (2002).

Kakkar, et al., "Role of tissue factor expression on tumour cell invasion and growth of experimental pancreatic adenocarcinoma," British Journal of Surgery, 86: 890-894 (1999).

Trisha Gura, "Systems for Identifying New Drugs are Often Faulty," Science, 273: 1041-1042 (1997).

http:// www.ncbi.nlm.nih.gov/entrez/query - cancer.

* cited by examiner

Fig. 1

```
                                                                                      60
CNTO859 HC   (1)  QVQLVESGGGVVQPGRSLRLSCKASGFNIKDYYMHWVRQAPGKGLEWIGLIDPENGNTIY
CNTO860 HC   (1)  QVQLVESGGGVVQPGRSLRLSCKASGFNIKDYYMHWVRQAPGKGLEWIGLIDPENGNTIY
                                                                                     120
CNTO859 HC  (61)  DPKFQGRFTISADNSKNTLFLQMDSLRPEDTAVYYCARDNSYYFDYWGQGTPVTVSSAST
CNTO860 HC  (61)  DPKFQGRFTISADNSKNTLFLQMDSLRPEDTAVYYCARDNSYYFDYWGQGTPVTVSSAST
                                                                                     180
CNTO859 HC (121)  KGPSVFPLAPCSRSTSESTAALGCLVKDYFPEPVTVSWNSGALTSGVHTFPAVLQSSGLY
CNTO860 HC (121)  KGPSVFPLAPSSKSTSGGTAALGCLVKDYFPEPVTVSWNSGALTSGVHTFPAVLQSSGLY
                                                                                     240
CNTO859 HC (181)  SLSSVVTVPSSSLGTKTYTCNVDHKPSNTKVDKRVESK---YGPPCPSCPAPEFLGGPSV
CNTO860 HC (181)  SLSSVVTVPSSSLGTQTYICNVNHKPSNTKVDKKVEPKSCDKTHTCPPCPAPELLGGPSV
                                                                                     300
CNTO859 HC (241)  FLFPPKPKDTLMISRTPEVTCVVVDVSQEDPEVQFNWYVDGVEVHNAKTKPREEQFNSTY
CNTO860 HC (241)  FLFPPKPKDTLMISRTPEVTCVVVDVSHEDPEVKFNWYVDGVEVHNAKTKPREEQYNSTY
                                                                                     360
CNTO859 HC (298)  RVVSVLTVLHQDWLNGKEYKCKVSNKGLPSSIEKTISKAKGQPREPQVYTLPPSQEMTK
CNTO860 HC (301)  RVVSVLTVLHQDWLNGKEYKCKVSNKALPAPIEKTISKAKGQPREPQVYTLPPSRDELTK
                                                                                     420
CNTO859 HC (358)  NQVSLTCLVKGFYPSDIAVEWESNGQPENNYKTTPPVLDSDGSFFLYSRLTVDKSRWQEG
CNTO860 HC (361)  NQVSLTCLVKGFYPSDIAVEWESNGQPENNYKTTPPVLDSDGSFFLYSKLTVDKSRWQQG
                                        447
CNTO859 HC (418)  NVFSCSVMHEALHNHYTQKSLSLSLGK
CNTO860 HC (421)  NVFSCSVMHEALHNHYTQKSLSLSPGK
```

*Fig. 2*
*a*
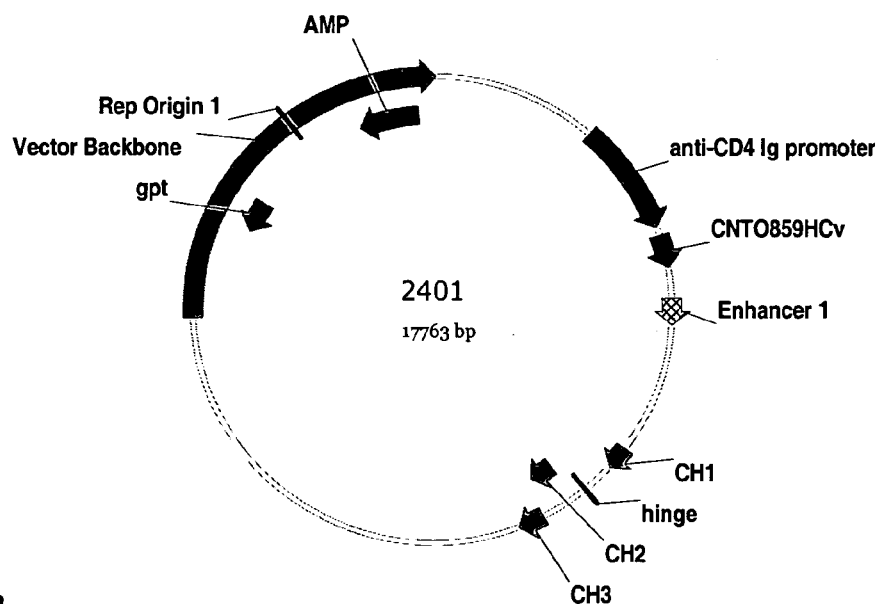
*b*
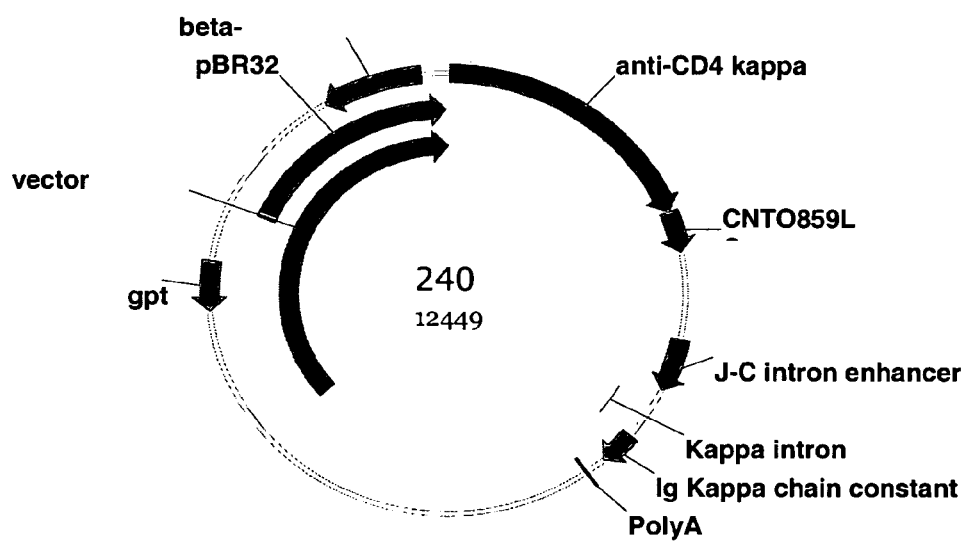

SEQUENCE LISTING

<160> NUMBER OF SEQ ID NOS: 22

<210> SEQ ID NO 1
<211> LENGTH: 1341
<212> TYPE: DNA
<213> ORGANISM: humanized

<400> SEQUENCE: 1

```
caagttcagc tggtggagtc tggaggagga gtagtacaac ctggaaggtc actgagactg      60
tcttgtaagg ctagtggatt caatatcaag gactattata tgcactgggt cagacaagct     120
cctggaaaag gactcgagtg gataggttta attgatcctg agaatggtaa cacgatatat     180
gatcccaagt tccaaggaag attcacaatt tctgcagaca actctaagaa tacactgttc     240
ctgcagatgg actcactcag acctgaggat acagcagtct actattgtgc tagagataac     300
agttattact tcgactactg gggccaagga acaccagtca ccgtgagctc agcctccacc     360
aagggcccat cggtcttccc cctggcaccc tcctccaaga gcacctctgg gggcacagcg     420
gccctgggct gcctggtcaa ggactacttc cccgaaccgg tgacggtgtc gtggaactca     480
ggcgccctga ccagcggcgt gcacaccttc ccggctgtcc tacagtcctc aggactctac     540
tccctcagca gcgtggtgac cgtgccctcc agcagcttgg gcacccagac ctacatctgc     600
aacgtgaatc acaagcccag caacaccaag gtggacaaga agttgagcc caaatcttgt     660
gacaaaactc acacatgccc accgtgccca gcacctgaac tcctgggggg accgtcagtc     720
ttcctcttcc ccccaaaacc caaggacacc ctcatgatct cccggacccc tgaggtcaca     780
tgcgtggtgg tggacgtgag ccacgaagac cctgaggtca agttcaactg gtacgtggac     840
ggcgtggagg tgcataatgc caagacaaag ccgcgggagg agcagtacaa cagcacgtac     900
cgggtggtca gcgtcctcac cgtcctgcac caggactggc tgaatggcaa ggagtacaag     960
tgcaaggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa a                                              1341
```

<210> SEQ ID NO 2
<211> LENGTH: 447
<212> TYPE: PRT
<213> ORGANISM: humanized
<220> FEATURE:
<221> NAME/KEY: MUTAGEN
<222> LOCATION: (234)..(235)
<223> OTHER INFORMATION: ala/ala

<400> SEQUENCE: 2

```
Gln Val Gln Leu Val Glu Ser Gly Gly Gly Val Val Gln Pro Gly Arg
1               5                   10                  15

Ser Leu Arg Leu Ser Cys Lys Ala Ser Gly Phe Asn Ile Lys Asp Tyr
            20                  25                  30

Tyr Met His Trp Val Arg Gln Ala Pro Gly Lys Gly Leu Glu Trp Ile
        35                  40                  45
```

```
Gly Leu Ile Asp Pro Glu Asn Gly Asn Thr Ile Tyr Asp Pro Lys Phe
 50                  55                  60

Gln Gly Arg Phe Thr Ile Ser Ala Asp Asn Ser Lys Asn Thr Leu Phe
 65                  70                  75                  80

Leu Gln Met Asp Ser Leu Arg Pro Glu Asp Thr Ala Val Tyr Tyr Cys
                 85                  90                  95

Ala Arg Asp Asn Ser Tyr Tyr Phe Asp Tyr Trp Gly Gln Gly Thr Pro
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 3
<211> LENGTH: 645
<212> TYPE: DNA
```

<213> ORGANISM: humanized

<400> SEQUENCE: 3

```
gatatccaaa tgacacaatc tccttcttct ctaagtgctt ctgtcggaga tagagtaaca      60
attacatgta aggcgagtca ggacattaga aagtatttaa actggtatca gcaaaaacct    120
gggaaggctc ctaagctact gatttattat gcaacaagtt tggcagatgg agtaccttct    180
agattttctg gttctggctc tggaacagac tacacattca caatttcttc tctccaacct    240
gaggacattg ctacatacta ctgcctacaa catggtgaga gtccgtatac atttggacaa    300
ggaacaaaac tagagatcac acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645
```

<210> SEQ ID NO 4
<211> LENGTH: 214
<212> TYPE: PRT
<213> ORGANISM: humanized

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Arg Lys Tyr
            20                  25                  30

Leu Asn Trp Tyr Gln Gln Lys Pro Gly Lys Ala Pro Lys Leu Leu Ile
        35                  40                  45

Tyr Tyr Ala Thr Ser Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln His Gly Glu Ser Pro Tyr
                85                  90                  95

Thr Phe Gly Gln Gly Thr Lys Leu Glu Ile Thr Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 117

```
<212> TYPE: PRT
<213> ORGANISM: humanized

<400> SEQUENCE: 5

Gln Val Gln Leu Val Glu Ser Gly Gly Val Val Gln Pro Gly Arg
1               5                   10                  15

Ser Leu Arg Leu Ser Cys Lys Ala Ser Gly Phe Asn Ile Lys Asp Tyr
                20                  25                  30

Tyr Met His Trp Val Arg Gln Ala Pro Gly Lys Gly Leu Glu Trp Ile
            35                  40                  45

Gly Leu Ile Asp Pro Glu Asn Gly Asn Thr Ile Tyr Asp Pro Lys Phe
    50                  55                  60

Gln Gly Arg Phe Thr Ile Ser Ala Asp Asn Ser Lys Asn Thr Leu Phe
65                  70                  75                  80

Leu Gln Met Asp Ser Leu Arg Pro Glu Asp Thr Ala Val Tyr Tyr Cys
                85                  90                  95

Ala Arg Asp Asn Ser Tyr Tyr Phe Asp Tyr Trp Gly Gln Gly Thr Pro
            100                 105                 110

Val Thr Val Ser Ser
            115

<210> SEQ ID NO 6
<211> LENGTH: 108
<212> TYPE: PRT
<213> ORGANISM: humanized

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Arg Lys Tyr
                20                  25                  30

Leu Asn Trp Tyr Gln Gln Lys Pro Gly Lys Ala Pro Lys Leu Leu Ile
            35                  40                  45

Tyr Tyr Ala Thr Ser Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln His Gly Glu Ser Pro Tyr
                85                  90                  95

Thr Phe Gly Gln Gly Thr Lys Leu Glu Ile Thr Arg
            100                 105

<210> SEQ ID NO 7
<211> LENGTH: 5
<212> TYPE: PRT
<213> ORGANISM: Mus sp.

<400> SEQUENCE: 7

Asp Tyr Tyr Met His
1               5

<210> SEQ ID NO 8
<211> LENGTH: 17
<212> TYPE: PRT
<213> ORGANISM: Mus sp.

<400> SEQUENCE: 8

Leu Ile Asp Pro Glu Asn Gly Asn Thr Ile Tyr Asp Pro Lys Phe Gln
1               5                   10                  15
```

Gly

<210> SEQ ID NO 9
<211> LENGTH: 8
<212> TYPE: PRT
<213> ORGANISM: Mus sp.

<400> SEQUENCE: 9

Asp Asn Ser Tyr Tyr Phe Asp Tyr
1               5

<210> SEQ ID NO 10
<211> LENGTH: 11
<212> TYPE: PRT
<213> ORGANISM: Mus sp.

<400> SEQUENCE: 10

Lys Ala Ser Gln Asp Ile Arg Lys Tyr Leu Asn
1               5                   10

<210> SEQ ID NO 11
<211> LENGTH: 7
<212> TYPE: PRT
<213> ORGANISM: Mus sp.

<400> SEQUENCE: 11

Tyr Ala Thr Ser Leu Ala Asp
1               5

<210> SEQ ID NO 12
<211> LENGTH: 9
<212> TYPE: PRT
<213> ORGANISM: Mus sp.

<400> SEQUENCE: 12

Leu Gln His Gly Glu Ser Pro Tyr Thr
1               5

<210> SEQ ID NO 13
<211> LENGTH: 15
<212> TYPE: DNA
<213> ORGANISM: Mus sp.

<400> SEQUENCE: 13
gactattata tgcac                                           15

<210> SEQ ID NO 14
<211> LENGTH: 51
<212> TYPE: DNA
<213> ORGANISM: Mus sp.

<400> SEQUENCE: 14
ttaattgatc ctgagaatgg taacacgata tatgatccca agttccaagg a    51

<210> SEQ ID NO 15
<211> LENGTH: 24
<212> TYPE: DNA
<213> ORGANISM: Mus sp.

<400> SEQUENCE: 15
gataacagtt attacttcga ctac                                 24

<210> SEQ ID NO 16

-continued

```
<211> LENGTH: 33
<212> TYPE: DNA
<213> ORGANISM: Mus sp.

<400> SEQUENCE: 16
aaggcgagtc aggacattag aaagtattta aac                                    33

<210> SEQ ID NO 17
<211> LENGTH: 21
<212> TYPE: DNA
<213> ORGANISM: Mus sp.

<400> SEQUENCE: 17
tatgcaacaa gtttggcaga t                                                 21

<210> SEQ ID NO 18
<211> LENGTH: 27
<212> TYPE: DNA
<213> ORGANISM: Mus sp.

<400> SEQUENCE: 18
ctacaacatg gtgagagtcc gtataca                                           27

<210> SEQ ID NO 19
<211> LENGTH: 15
<212> TYPE: DNA
<213> ORGANISM: Artificial
<220> FEATURE:
<223> OTHER INFORMATION: PCR primer

<400> SEQUENCE: 19
gccaccatgg aatgg                                                        15

<210> SEQ ID NO 20
<211> LENGTH: 39
<212> TYPE: DNA
<213> ORGANISM: Artificial
<220> FEATURE:
<223> OTHER INFORMATION: PCR primer

<400> SEQUENCE: 20
ggtcagtggc actcgagtcc attcaagatc ttcgaaccg                              39

<210> SEQ ID NO 21
<211> LENGTH: 45
<212> TYPE: DNA
<213> ORGANISM: Artificial
<220> FEATURE:
<223> OTHER INFORMATION: PCR primer

<400> SEQUENCE: 21
gtgagatctg aaatacatca gatcaccatg ggtgtgccaa ctcag                       45

<210> SEQ ID NO 22
<211> LENGTH: 43
<212> TYPE: DNA
<213> ORGANISM: Artificial
<220> FEATURE:
<223> OTHER INFORMATION: PCR primer

<400> SEQUENCE: 22
ccttgttttg atctctagtg tgcattcatt cgaacagctg aga                         43
```

ANTI-TISSUE FACTOR ANTIBODIES AND COMPOSITIONS

CROSS REFERENCE TO RELATED APPLICATION

This application is a continuation-in-part of U.S. application Ser. No. 10/855,664, filed May 27, 2004, which claims the benefit of U.S. provisional application No. 60/475,174 filed May 30, 2003.

BACKGROUND OF THE INVENTION

1. Field of the Invention

The present invention relates to antibodies which bind to human tissue factor, including specified portions or variants thereof. The antibodies of the invention have the ability to interact with effector cells to activate innate immunity in addition to their human tissue factor neutralizing activity and are thus particularly useful in methods for treating tumor cells. The invention also relates to nucleic acids encoding such anti-tissue factor antibodies, complementary nucleic acids, vectors, host cells, and methods of making and using thereof, including therapeutic formulations, administration and devices.

2. Related Art

Tissue Factor (TF)

The coagulation of blood involves a cascading series of reactions leading to the formation of fibrin. The coagulation cascade consists of two overlapping pathways, both of which are required for hemostasis. The intrinsic pathway comprises protein factors present in circulating blood, while the extrinsic pathway requires tissue factor (TF), which is expressed on the cell surface of a variety of tissues in response to vascular injury (Davie et al., 1991, Biochemistry 30:10363). When exposed to blood, TF sets in motion a potentially explosive cascade of activation steps that result in the formation of an insoluble fibrin clot. TF has been investigated as a target for anticoagulant therapy.

TF is a single chain, 263 amino acid membrane glycoprotein that functions as a receptor for factor VII and VIIa and thereby initiates the extrinsic pathway of the coagulation cascade in response to vascular injury. TF is a transmembrane cell surface receptor which serves as the receptor as well as the cofactor for factor VIIa, forming a proteolytically active TF:VIIa complex on cell surfaces (Ruf et al, (1992) J. Biol. Chem 267:6375-6381). In addition to its role in maintaining hemostasis, excess TF has been implicated in pathogenic conditions. Specifically, the synthesis and cell surface expression of TF has been implicated in vascular disease (Wilcox et al., 1989, Proc. Natl. Acad. Sci, 86:2839) and gram-negative septic shock (Warr et al., 1990, Blood 75:1481).

TF Antagonists

Various anti-TF antibodies are known. For example, Carson et al, (1987, Blood 70:490-493) discloses a hybridoma producing monoclonal antibody prepared by immunizing mice with TF purified by affinity chromatography on immobilized factor VII. Ruf et al, (1991, Thrombosis and Haemostasis 66:529) characterized the anticoagulant potential of murine monoclonal antibodies against human TF. The ability of monoclonal antibodies that target the FVII binding site on TF, is dependent on their ability to compete with FVII for binding to TF and formation of the TF/VIIa complex, which is rapidly formed when TF contacts plasma. Such antibodies were thus relatively slow inhibitors of TF in plasma. One monoclonal antibody, TF8-5G9, was capable of inhibiting the TF/VIIa complex, thus providing an immediate anticoagulant effect in plasma. This antibody is disclosed in U.S. Pat. Nos. 6,001,978, 5,223,427, and 5,110,730. Ruf et al, suggested (supra) that mechanisms that inactivate the TF/VIIa complex, rather than prevent its formation, may provide strategies for interruption of coagulation in vivo. In contrast to other antibodies that inhibit factor VII binding to TF, TF8-5G9 shows only subtle and indirect effects on factor VII or factor VIIa binding to the receptor. TF8-5G9 binds to the extracellular domain of TF with a nanomolar binding constant to block the formation of the TF:F.VIIa:F.X ternary initiation complex (Huang et al, J. Mol. Biol. 275:873-894 1998).

Anti-TF monoclonal antibodies have been shown to inhibit TF activity in various species (Morissey et al., 1988, Thromb. Res. 52:247-260) and neutralizing anti-TF antibodies have been shown to prevent death in a baboon model of sepsis (Taylor et al, Circ. Shock, 33:127 (1991)), and attenuate endotoxin induced DIC in rabbits (Warr et al, (1990) Blood 75:1481).

WO 96/40921 discloses CDR-grafted anti-TF antibodies derived from the TF8-5G9 antibody. Other humanized or human anti-TF antibodies are disclosed in Presta et al, Thromb Haemost 85:379-389 (2001), EP1069185, WO 01/70984 and WO03/029295.

The Role of TF in Cancer

Tissue factor (TF) is a cell surface receptor best known for its role in initiating blood coagulation upon injury. Tissue factor is also overexpressed on a variety of malignant tumors and isolated human tumor cell lines, suggesting a role in tumor growth and survival. TF is not produced by healthy endothelial cells lining normal blood vessels but is expressed on these cells in tumor vessels. It appears to play a role in both vasculogenesis, the formation of new blood vessels in the developing animal and in angiogenesis, the sprouting of new capillaries from existing arteries, in normal and malignant adult tissues.

Aberrant expression of TF on endothelial and tumor cells in a variety of breast, colorectal, lung and pancreatic cancers has been linked to an increase in tumor microvessel density and upregulated VEGF expression. Tumor cells over expressing TF are also thought to be responsible for the thrombotic complications associated with cancer. Thus there is a rationale for the inhibition of tissue factor in the treatment of cancer.

WO94/05328 discloses the use of anti-TF antibodies to inhibit the onset and progression of metastasis by abolishing the prolonged adherence of metastazing cells in the microvasculature thereby inhibiting metastasis, but does not disclose any effect on the growth of established tumor cells. Given the complexity in the factors regulating tumor vascularization as well as the incomplete understanding of the role of tissue factor as a receptor mediating cellular growth in both tumor growth and wound healing, it is possible that blockade of TF could play either a critical or a redundant role in the pathogenesis of cancer or other diseases characterized by inappropriate angiogenic activity. Inhibition or targeting of TF may therefore be a useful anti-tumor strategy that could affect the survival of TF overexpressing tumor cells directly by inhibiting TF mediated cellular signaling or other activities. In addition, this approach may prevent tumor growth indirectly via an antiangiogenic mechanism by inhibiting the growth or function of TF expressing intra-tumoral endothelial cells.

TF and Angiogenesis

Angiogenesis is the process of generating new capillary blood vessels, and results from activated proliferation of endothelial cells. Neovascularization is tightly regulated, and occurs only during embryonic development, tissue remodeling, wound healing and periodic cycle of corpus luteum development (Folkman and Cotran, Relation of vascular proliferation to tumor growth, Int. Rev. Exp. Pathol.'16, 207-248 (1976)).

There is now considerable evidence that tumor growth and cancer progression requires angiogenesis and neovascularization, blood vessel growth and extension, in order to provide tumor tissue with nutrients and oxygen, to carry away waste products and to act as conduits for the metastasis of tumor cells to distant sites (Folkman, et al. N Engl J Med 285: 1181-1186, 1971 and Folkman, et al. N Engl J Med 333: 1757-1763, 1995). Nevertheless, tissue and tumor angiogenesis and neovascularization represent complex processes mediated by the interplay of cellularly produced factors: including TNFalpha, VEGF, and tissue factor. Studies show that the pathways leading to upregulation of VEGF and TF overlap (Chen J. et al. (2001) Thromb. Haemost. 86-334-5), two major players in the initiation of new blood vessel formation.

Endothelial cells normally proliferate much more slowly than other types of cells in the body. However, if the proliferation rate of these cells becomes unregulated, pathological angiogenesis can result. Pathological angiogenesis is involved in many diseases. For example, cardiovascular diseases such as angioma, angiofibroma, vascular deformity, atherosclerosis, synechia and edemic sclerosis; and opthalmological diseases such as neovascularization after cornea implantation, neovascular glaucoma, diabetic retinopathy, angiogenic corneal disease, macular degeneration, pterygium, retinal degeneration, retrolental fibroplasias, and granular conjunctivitis are related to angiogenesis. Chronic inflammatory diseases such as arthritis; dermatological diseases such as psoriasis, telangiectasis, pyogenic granuloma, seborrheic dermatitis, venous ulcers, acne, rosacea (acne rosacea or erythematosa), warts (verrucas), eczema, hemangiomas, lymphangiogenesis are also angiogenesis-dependent.

Vision can be impaired or lost because of various ocular diseases in which the vitreous humor is infiltrated by capillary blood. Diabetic retinopathy can take one of two forms, non-proliferative or proliferative. Proliferative retinopathy is characterized by abnormal new vessel formation (neovascularization), which grows on the vitreous surface or extends into the vitreous cavity. In advanced disease, neovascular membranes can occur, resulting in a traction retinal detachment. Vitreous hemorrhages may result from neovascularization. Visual symptoms vary. A sudden severe loss of vision can occur when there is intravitreal hemorrhage. Visual prognosis with proliferative retinopathy is more guarded if associated with severe retinal ischemia, extensive neovascularization, or extensive fibrous tissue formation. Macular degeneration, likewise takes two forms, dry and wet. In exudative macular degeneration (wet form), which is much less common, there is formation of a subretinal network of choroidal neovascularization often associated with intraretinal hemorrhage, subretinal fluid, pigment epithelial detachment, and hyperpigmentation. Eventually, this complex contracts and leaves a distinct elevated scar at the posterior pole. Both forms of age-related macular degeneration are often bilateral and are preceded by drusen in the macular region. Another cause of loss of vision related to angiogenic etiologies are damage to the iris. The two most common situations that result in the iris being pulled up into the angle are contraction of a membrane such as in neovascular glaucoma in patients with diabetes or central retinal vein occlusion or inflammatory precipitates associated with uveitis pulling the iris up into the angle (Ch. 99. The Merck Manual 17th Ed. 1999).

Rheumatoid arthritis, an inflammatory disease, also results in inappropriate angiogenesis. The growth of vascular endothelial cells in the synovial cavity is activated by the inflammatory cytokines, and results in cartilage destruction and replacement with pannus in the articulation (Koch A K, Polverini P J and Leibovich S J. Arthritis Rheum. 29, 471-479 (1986); Stupack D G, Storgard C M and Cheresh D A, Braz. J. Med. Biol. Res., 32, 578-581(1999); Koch A K, Arthritis Rheum, 41, 951 962(1998)).

Psoriasis is caused by uncontrolled proliferation of skin cells. Fast growing cells require sufficient blood supply, and abnormal angiogenesis is induced in psoriasis (Folkman J., J. Invest. Dermatol., 59, 40-48(1972)).

Antibody Properties

IgG1 and IgG4 antibody isotypes differ in their ability to mediate complement dependent cytotoxicity (CDC) and antibody-dependent cellular cytotoxicity (ADCC). CDC is the lysing of a target in the presence of complement. The complement activation pathway is initiated by the binding of the first component of the complement system (C1q) to a molecule complexed with a cognate antigen. IgG1 is a strong inducer of the complement cascade and subsequent CDC activity, while IgG4 has little complement-inducing activity.

ADCC is a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The IgG1 isotype subclass binds with high affinity to the Fc receptor and contributes to ADCC while IgG4 binds only weakly. The relative inability of IgG4 to activate effector functions is drawback in those applications such as oncology where cell killing is a desirable characteristic of the antibody.

There remains a need in the art for variant structures of anti-TF antibodies with properties optimized for specific clinical indications. For example, optimizing ADCC and CDC antibody functions is generally desirable for oncology indications. Other potential uses for anti-TF antibodies with enhanced ADCC activity include therapy for age related macular degeneration or other angiogenesis related conditions in which endothelial cells in aberrant blood vessels may express TF and can be targeted by ADCC. The inventors of this application have produced variant anti-TF antibody structures designed to meet these needs.

SUMMARY OF THE INVENTION

The present invention provides isolated anti-tissue factor antibodies, immunoglobulins, cleavage products and other specified portions and variants thereof having enhanced ADCC activity, as well as anti-tissue factor antibody compositions, encoding or complementary nucleic acids, vectors, host cells, compositions, formulations, devices, transgenic animals, transgenic plants, and methods of making and using thereof. The antibodies of the invention bind human tissue factor and demonstrate enhanced ADCC activity. Accordingly, the antibodies can be used in a variety of methods for diagnosing, treating, and/or preventing diseases involving tissue factor, where enhanced ADCC activity is desirable such as cancer.

Thus, in one embodiment, the present invention provides at least one isolated tissue factor antibody as described herein. In one embodiment, the antibody according to the present invention includes any protein or peptide containing molecule that comprises at least a portion of a complementarity determining region (CDR) of a heavy or light chain or a ligand binding portion thereof derived from the antibody designated TF8-5G9, in combination with a heavy chain or light chain variable region, a framework region, and a heavy chain or light chain constant region that is capable of interacting with effector cells or molecules to activate innate immunity (e.g. complement lysis, NK cell killing oropsonization/phagocytosis by macrophages) and thus imparts ADCC activity to the antibody, or any portion thereof, that can be incorporated into an antibody of the present invention. The antibody CNTO 860 described herein is a human tissue factor antibody derived from the TF8-5G9 antibody in which the IgG4 Fc region was exchanged with an IgG1 Fc by recloning the humanized variable domain into a vector containing the desired heavy chain constant regions; CH1, CH2 and CH3. The IgG1 antibody exhibits similar antigen binding and coagulation inhibiting properties as the IgG4 version, but demonstrates markedly enhanced ADCC activity and is more potent at inhibiting the growth of orthotopic MDA-MB-231 human breast carcinoma xenografts.

Particular therapeutic antibodies of the invention include human monoclonal antibody CNTO 860, and functionally equivalent antibodies which have the human heavy chain and human light chain amino acid sequences as set forth in SEQ ID NO: 2 and SEQ ID NO: 4 respectively, and conservative modifications thereof. The antibody amino acid sequence can further optionally comprise at least one specified substitution, insertion or deletion as described herein or as known in the art.

Other particular antibodies of the invention include human monoclonal antibodies which bind to an epitope defined by antibody CNTO 860, and/or which compete for binding to tissue factor with antibody CNTO 860, or which have other functional binding characteristics exhibited by antibody CNTO 860, and which compete for binding to Fc receptors with CNTO 860. Such antibodies include, for example, those which bind to tissue factor with dissociation constant (KD) of 1-2 nanomolar or less and which have an apparent binding affinity for FcγRII on U937 cells of 40-100 nanomolar or less in a Fc receptor competition binding assay.

Isolated antibodies of the invention include those having antibody isotypes with ADCC activity greater than exhibited by IgG4, such as IgG1, (e.g., IgG1κ and IgG1λ), IgG2, and IgG3, or hybrid isotypes containing altered residues at specific residues in the Fc domains. The antibodies can be full-length antibodies (e.g., IgG1) or can include only an antigen-binding portion and an Fc portion or domain capable of eliciting effector functions including ADCC, complement activation, and C1q binding.

The present invention also provides at least one isolated human tissue factor antibody as described herein, wherein:
 the antibody competes with CNTO 860 for binding to human tissue factor;
 the antibody inhibits the TF:FVIIa complex;
 has an affinity to TF on MDA-MB-231 human breast carcinoma cells as measured by flow cytometry equivalent to CNTO 860;
 can block in vivo coagulation of human plasma in a prothrombin assay at a concentration equivalent to CNTO 860; and
 shows killing of MDA-MB-231 cells and HCT116 equivalent to CNTO 860 in a chromium release ADCC assay.

A tissue factor antibody can thus be screened for such corresponding activities according to known methods.

The present invention provides, in one aspect, isolated nucleic acid molecules comprising, complementary, or hybridizing to, a polynucleotide encoding the specific tissue factor antibodies described herein. Such nucleic acid molecules include those encoding all or a portion of a monoclonal tissue factor antibody as described herein, as well as recombinant expression vectors which include such nucleic acids, and host cells transfected with such vectors. Methods of producing the antibodies by culturing such host cells are also encompassed by the invention. Particular nucleic acids provided by the invention comprise the nucleotide sequences shown in SEQ ID NOs: 1 and SEQ ID NOs: 3, which encode the heavy and light chains, respectively, of human tissue factor antibody CNTO 860. The present invention further provides recombinant vectors comprising said anti-tissue factor antibody nucleic acid molecules, host cells containing such nucleic acids and/or recombinant vectors, as well as methods of making and/or using such antibody nucleic acids, vectors and/or host cells.

The present invention also provides at least one method for expressing at least one tissue factor antibody as described herein, in a host cell, comprising culturing a host cell as described herein under conditions wherein at least one tissue factor antibody is expressed in detectable and/or recoverable amounts.

The present invention also provides at least one composition comprising (a) an isolated anti-tissue factor antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition.

The present invention further provides at least one tissue factor antibody method or composition, for administering a therapeutically effective amount to modulate or treat at least one tissue factor related condition in a cell, tissue, organ, animal or patient and/or, prior to, subsequent to, or during a related condition, as known in the art and/or as described herein. The compositions include, for example, pharmaceutical and diagnostic compositions/kits, comprising a pharmaceutically acceptable carrier and at least one tissue factor antibody. In one embodiment, the composition comprises a combination of human antibodies or antigen-binding portions thereof, preferably each of which binds to a distinct epitope. For example, a pharmaceutical composition comprising a monoclonal antibody that mediates highly effective killing of target cells in the presence of effector cells can be combined with a monoclonal antibody that inhibits tissue factor activity and signaling in tumor angiogenesis, metastasis and growth. Thus, the combination provides multiple therapies tailored to provide the maximum therapeutic benefit. Compositions, e.g., pharmaceutical compositions, comprising a combination of at least one human tissue factor-antibody, or antigen-binding portion thereof, and at least one bispecific or multispecific molecule of the invention, are also within the scope of the invention.

In yet another aspect of the invention, the tissue factor antibodies are derivatized, linked to or co-expressed with another functional molecule, e.g., another peptide or protein (e.g., an Fab' fragment). For example, an antibody or antigen-binding portion of the invention can be functionally linked (e.g., by chemical coupling, genetic fusion, noncovalent association or otherwise) to one or more other molecular entities, such as another antibody (e.g., to produce a bispecific or a multispecific antibody), a cytotoxin, a cellular ligand or an antigen. Accordingly, present invention encompasses a large variety of antibody conjugates, bi- and multispecific molecules, and fusion proteins, all of which bind to tissue factor expressing cells and which target other molecules to the cells, or which bind to tissue factor and to other molecules or cells.

Alternatively, antibodies of the invention can be co-administered with such therapeutic and cytotoxic agents, but not linked to them. They can be coadministered simultaneously with such agents (e.g., in a single composition or separately) or can be administered before or after administration of such agents. Such agents can include chemotherapeutic agents, such as dacarbazine, doxorubicin (adriamycin), cisplatin, bleomycin sulfate, carmustine, chlorambucil, cyclophosphamide hydroxyurea and combinations thereof. Antibodies of the invention also can be administered in conjunction with radiation therapy or hyperthermic therapy.

In yet another embodiment, the present invention provides a method for inhibiting the proliferation and/or growth of a cell expressing tissue factor and inducing killing of a cell expressing tissue factor, by contacting the cells with (e.g., administering to a subject) one or more antibodies of the invention and/or related therapeutic compositions, derivatives etc. containing the antibodies as described above. In a particular embodiment, the method comprises contacting cells expressing tissue factor either in vitro or in vivo with one or a combination of tissue factor antibodies of the invention in the presence of a human effector cell. The method can be employed in culture, e.g. in vitro or ex vivo (e.g., cultures comprising cells expressing tissue factor and effector cells). For example, a sample containing cells expressing tissue factor and effector cells can be cultured in vitro, and combined with an antibody of the invention.

Alternatively, the method can be performed in a subject, e.g., as part of an in vivo (e.g., therapeutic or prophylactic) protocol. For use in in vivo treatment and prevention of tissue factor mediated diseases, antibodies of the present invention are administered to patients (e.g., human subjects) at therapeutically effective dosages (e.g., to inhibit, eliminate or prevent growth of cells expressing tissue factor or to inhibit angiogenesis and thus inhibit the growth of cells where growth is mediated by angiogenesis) using any suitable route of administration for antibody-based clinical products as are well known in the art, such as by injection or infusion.

Accordingly, antibodies of the present invention can be used to treat and/or prevent a variety of tissue factor mediated diseases where ADCC activity and other effector functions leading to increased killing and removal of target cells is desirable by administering a suitable dosage (or series of dosages) of the antibodies to patients suffering from such diseases. Exemplary diseases that can be treated (e.g., ameliorated) or prevented using the methods and compositions of the invention include, but are not limited to, cancers, such as metastatic melanoma, prostate cancer, colon cancer, and renal carcinoma.

In a particular embodiment of the invention, the patient can be additionally treated with a chemotherapeutic agent, radiation, or an agent that modulates, e.g., enhances, the expression or activity of an Fc receptor, such as a cytokine. Typical cytokines for administration during treatment include granulocyte colony-stimulating fact or (G-CSF), granulocytemacrophage colony-stimulating factor (GM-CSF), interferon-y (IFN-y), and tumor necrosis factor (TNF). Typical therapeutic agents include, among others, anti-neoplastic agents such as dacarbazine, doxorubicin (adriamycin), cisplatin, bleomycin sulfate, carmustine, chlorambucil, cyclophosphamide, and hydroxyurea.

As exemplified herein, tissue factor antibodies can be obtained directly from hybridomas which express the antibody, or can be cloned and recombinantly expressed in a host cell, such as a transfectoma (e.g., a transfectoma consisting of immortalized CHO cells or lymphocytic cells). Accordingly, the present invention provides methods for producing monoclonal antibodies which bind to human tissue factor.

DESCRIPTION OF THE FIGURES

FIG. 1 is an alignment of the amino acid sequences of the mature heavy chains of CNTO 859 and CNTO 860.

FIG. 2 shows diagrams of the expression vectors for CNTO860 heavy chain, p2401 (a) and light chain (b).

FIG. 6 shows the tumor progression of MDA MB 231 xenografts as measured by volume in animals treated with either PBS, control human Ig or various dosages of CNTO 859. CNTO 859 was able to inhibit tumor growth at all concentrations. Tumor inhibition ranged from 90% at 0.1 mg/kg ($p=0.0012$ and $p=0.0106$, respectively, Wilcoxon two-sample test using t-distribution) to 95% at any concentration above that.

DETAILED DESCRIPTION OF THE INVENTION

The present invention provides isolated, recombinant and/or synthetic anti-tissue factor monoclonal antibodies having enhanced ADCC activity, as well as compositions and encoding nucleic acid molecules comprising at least one polynucleotide encoding such antibodies.

In order that the present invention may be more readily understood, certain terms are first defined. Additional definitions are set forth throughout the detailed description.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

Figure 13:
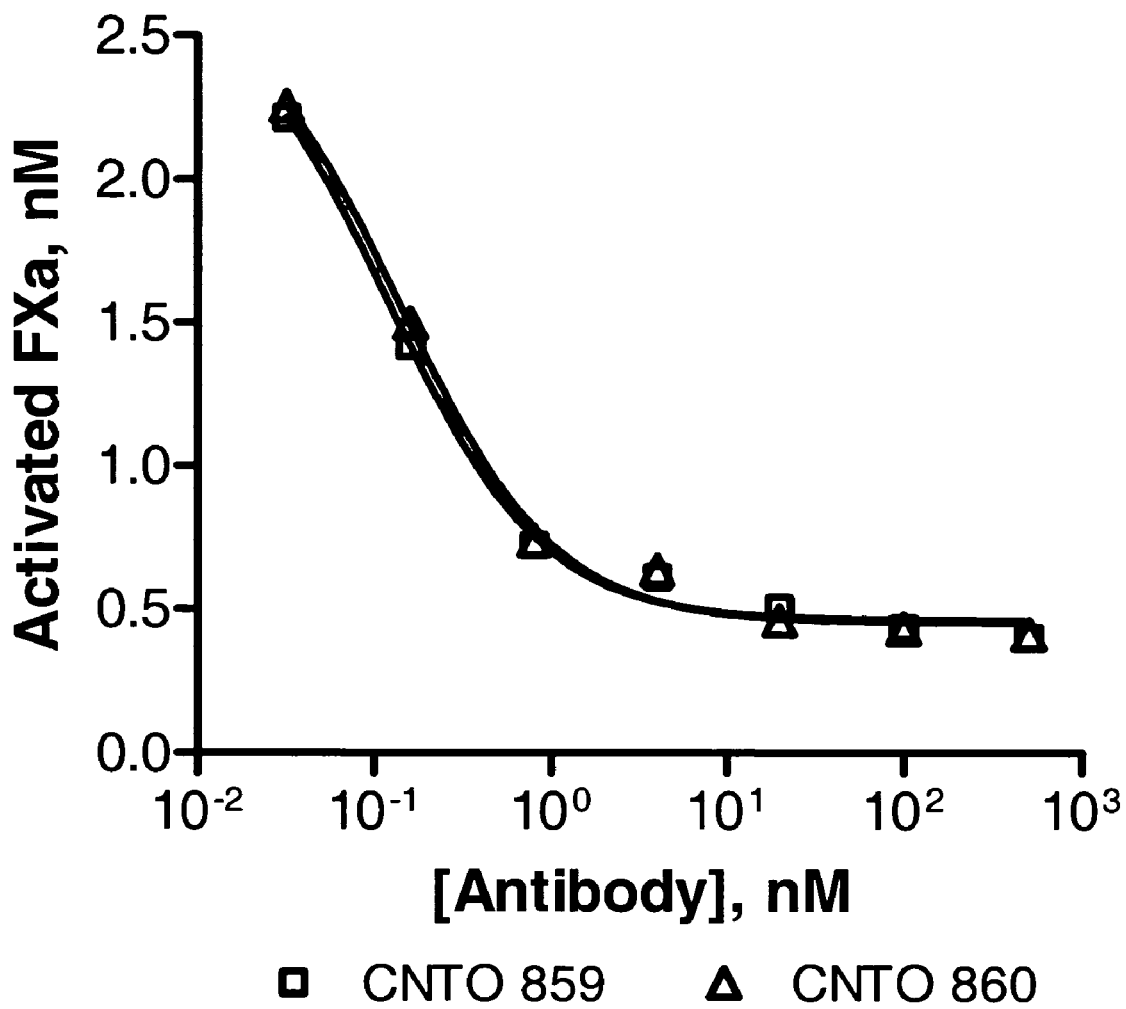
FIG. 13 is a graph showing the relationship between antibody concentration and the inhibition of Fxa activation.

The terms "tissue factor protein" and "mammalian tissue factor protein" are used to refer to a polypeptide having an amino acid sequence corresponding to a naturally occurring mammalian tissue factor or a recombinant tissue factor as described below. Naturally occurring TF includes human species as well as other animal species such as rabbit, rat, porcine, non human primate, equine, murine, and ovine tissue factor (see, for example, Hartzell et al., (1989) Mol. Cell. Biol., 9:2567-2573; Andrews et al., (1991) Gene, 98:265-269; and Takayenik et al., (1991) Biochem. Biophys. Res. Comm., 181:1145-1150). The amino acid sequence of human tissue factor is shown in FIG. 13 (SEQ ID NO: 13). The amino acid sequence of the other mammalian tissue factor proteins are generally known or obtainable through conventional techniques.

A "TF mediated or associated process or event", or equivalently, an "activity associated with TF", according to the present invention is any event which is mediated by the presence of TF. A "TF related disease or disorder" is meant to diseases or disorders which may be impacted through the inhibition of TF, particularly the inhibition of tumor growth on tissue factor expressing cells, but also includes other tissue factor mediated diseases such as chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, acute and chronic indications such as inflammation, septic shock, septicemia, hypotension, adult respiratory distress syndrome (ARDS), disseminated intravascular coagulopathy (DIC) and other diseases.

The term "ADCC activity" stands for antibody-dependent cell-mediated cytotoxicity and means the phenomenon of antibody-mediated target cell destruction by non-sensitized effector cells. The identity of the target cell varies, but it must have bound surface immunoglobulin G whose Fc portion is intact. The effector cell is a "killer" cell possessing Fc receptors. It may be a lymphocyte lacking conventional B- or T-cell markers, or a monocyte, macrophage, or polynuclear leukocyte, depending on the identity of the target cell. The reaction is complement independent. The ADCC activity of an antibody of the present invention is "enhanced", if its ability to demonstrate ADCC mediated cell killing surpasses the ability of an anti-TF IgG4 antibody, as determined in a standard in vivo or in vitro assay of cell killing, such as the assays discussed herein. Preferably, the anti-TF with enhanced ADCC activity achieves the same effect (prevention or inhibition of tumor cell growth) at a lower dose and/or in a shorter time than a reference IgG4 antibody. Preferably, the difference between the potency of an antibody within the scope of the present invention and a reference antibody is at least about 1-fold, more preferably at least about 2-fold, even more preferably at least about 3-fold, most preferably at least about 5-fold, as determined by side-by-side comparison in a selected standard chromium release ADCC assay.

"Antibody fragments" comprise a portion of a full length antibody, generally the antigen binding or variable domain thereof. Examples of antibody fragments include Fab, Fab', F(ab')2, and Fv fragments; diabodies; linear antibodies; single-chain antibody molecules; and multispecific antibodies formed from antibody fragments.

"Effector functions" of antibodies or antibody analogs as it is used herein are processes by which pathogens or abnormal cells, e.g. tumor cells, are destroyed and removed from the body. Innate and adaptive immune responses use most of the same effector mechanisms to eliminate pathogens including ADCC, CA (complement activation), C1q binding, and opsinization.

The terms "monoclonal antibody" or "monoclonal antibody composition" as used herein refer to a preparation of antibody molecules of single molecular composition. A monoclonal antibody composition displays a single binding specificity and affinity for a particular epitope. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567) The "monoclonal antibodies" may also be isolated from phage antibody libraries using the techniques described in Clackson et al., Nature 352:624-628 (199 1) and Marks et al., J. Mol. Biol. 222:581-597 (199 1), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567 and Morrison et al., Proc. Nat. Acad. Sci. USA 81:6851-6855 (1984)).

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region (which are also known as the complementarity determining regions or CDR) residues of the recipient are replaced by hypervariable region residues from a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. The humanized antibody optionally also will comprise at least a portion of an immunoglobulin constant region (Fc), typically that of a human I 0 immunoglobulin. For further details, see Jones et al., Nature 321:522-525 (1986); Reichmann et al., Nature 332:323-329 (1988); and Presta, Curr. Op. Struct. Biol. 2:593-596 (1992).

The term "recombinant antibody", as used herein, includes all antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody," as used herein, is intended to refer to an antibody which is substantially free of other antibodies having different antigenic specificities (e.g., an isolated antibody that specifically binds to tissue factor is substantially free of antibodies that specifically bind antigens other than tissue factor). An isolated antibody that specifically binds to an epitope, isoform or variant of human tissue factor may, however, have cross-reactivity to other related antigens, e.g., from other species (e.g., tissue factor species homologs). Moreover, an isolated antibody may be substantially free of other cellular material and/or chemicals. In one embodiment of the invention, a combination of "isolated" monoclonal antibodies having different specificities are combined in a well defined composition.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The term "native conformational epitope" or "native protein epitope" are used interchangeably herein, and include protein epitopes resulting from conformational folding of the integrin molecule which arise when amino acids from differing portions of the linear sequence of the integrin molecule come together in close proximity in 3 dimensional space. Such conformational epitopes are distributed on the extracellular side of the plasma membrane.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g. a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to tissue factor, and to other targets, such as Fc receptors on effector cells.

The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad Sci. USA 90:6444-6448; Poljak, R. J., et al. (I 994) Structure 2:1121-1123). Bispecific, heterospecific, heteroconjugate or similar antibodies can also be used that are monoclonal, preferably human or humanized, antibodies that have binding specificities for at least two different antigens. In the present case, one of the binding specificities is for at least one tissue factor protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121:210 (1986), each entirely incorporated herein by reference.

As used herein, the term "heteroantibodies" refers to two or more antibodies, antibody binding fragments (e.g., Fab), derivatives therefrom, or antigen binding regions linked together, at least two of which have different specificities. These different specificities include a binding specificity for an Fc receptor on an effector cell, and a binding specificity for an antigen or epitope on a target cell, e.g., a tumor cell.

As used herein, "specific binding" refers to antibody binding to a predetermined antigen. Typically, the antibody binds with a dissociation constant ($K_D$) of $10^{-7}$ M or less, and binds to the predetermined antigen with a $K_D$ that is at least twofold less than its $K_D$ for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen".

As used herein, the term "high affinity" for an IgG antibody refers to an antibody having a $K_D$ Of $10^{-8}$ M or less, more preferably $10^{-9}$ M or less and even more preferably $10^{-10}$ M or less. However, "high affinity" binding can vary for other antibody isotypes. For example, "high affinity" binding for an IgM isotype refers to an antibody having a $K_D$ of $10^{-7}$ M or less, more preferably $10^{-8}$ M or less. The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction, The term "$K_D$", as used herein, is intended to refer to the dissociation constant, which is obtained from the ratio of Kd to Ka (i. e. Kd/Ka) and is expressed as a molar concentration (M).

As used herein, "isotype" refers to the antibody class (IgA, IgD, IgE, IgG, or IgM) that is encoded by heavy chain constant region genes. Among human IgG isotypes there are four subclasses; IgG1, IgG2, IgG3 and IgG4 named in order of their natural abundance in serum starting from highest to lowest. IgA antibodies are found as two subclasses, IgA1 and IgA2. As used herein, "isotype switching" also refers to a change between IgG subclasses or subtypes.

The term "nucleic acid molecule", as used herein, is intended to include DNA molecules and RNA molecules. A nucleic acid molecule may be single-stranded or double-stranded, but preferably is double-stranded DNA. The term "isolated nucleic acid molecule," as used herein in reference to nucleic acids encoding antibodies or antibody portions (e.g., VH, VL, CDR3) that bind to tissue factor, is intended to refer to a nucleic acid molecule in which the nucleotide sequences encoding the antibody or antibody portion are free of other nucleotide sequences encoding antibodies or antibody portions that bind antigens other than tissue factor, which other sequences may naturally flank the nucleic acid in human genomic DNA. In one embodiment, the anti-tissue factor antibody, or portion thereof, includes the nucleotide or amino acid sequence of CNTO 860.

As disclosed and claimed herein, the invention includes antibodies having "conservative sequence modifications" of the sequences set forth in SEQ ID NOs: 2 and 4, i.e., amino acid sequence modifications which do not significantly affect or alter the binding characteristics of the antibody encoded by the nucleotide sequence or containing the amino acid sequence. Such conservative sequence modifications include amino acid substitutions, additions and deletions. Codon substitutions of the coding sequence are often desirable when the expression system for the antibody is altered, e.g. from a murine myeloma cell line to an *E.coli* system. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in a tissue factor antibody is preferably replaced with another amino acid residue from the same side chain family.

Modifications can be introduced into the nucleotide sequences of SEQ ID NOs: 1 and 3 by standard techniques known in the art, such as site-directed mutagenesis and PCR-mediated mutagenesis. Codon substitutions in SEQ ID NOs: 1 and 3 which do not alter the sequence of the encoded protein are also included in the present invention. Alternatively, in another embodiment, mutations can be introduced randomly along all or part of a anti-tissue factor antibody coding sequence, such as by saturation mutagenesis, and the resulting modified anti-tissue factor antibodies can be screened for binding activity.

Accordingly, antibodies encoded by the nucleotide sequences disclosed herein and/or containing the amino acid sequences disclosed herein (i.e., SEQ ID NOs: 1-4) include substantially similar antibodies encoded by or containing similar sequences which have been conservatively modified. Further discussion as to how such substantially similar antibodies can be generated based on the sequences disclosed herein as SEQ ID NOs: 2 and 4 is provided below. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (Comput. AppL Biosci., 4:11-17 (1988)) which has been incorporated into the ALIGN program (version 2.0), using a PAM 1 20 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (www.gcg.com), using either a Blossum 62 matrix or a PAM2 5 0 matrix, and a gap weight of 16, 14, 12, 10, 8, 6, or 4 and a length weight of 1, 2, 3, 4, 5, or 6. The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (I 990) J Mol. Biol. 215.403-1 0. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389 When utilizing BLAST and Gapped BLAST programs, the default parameters of the respective programs (e.g., XBLAST and NBLAST) can be used. See http://www.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof, may be mutated in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, CHO cells and lymphocytic cells.

As used herein, the term "subject" includes any human or nonhuman animal. The term "nonhuman animal" includes all vertebrates, e.g., mammals and nonmammals, such as non-human primates, sheep, dog, cow, chickens, amphibians, reptiles, etc.

Citations

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

1. Production of Antibodies

Anti-tissue factor antibodies of the present invention can be optionally produced by a variety of techniques, including conventional monoclonal antibody techniques, e.g., the standard somatic cell hybridization technique of Kohler and Milstein (1975) Nature 256:495. A variety of cell lines, mixed cell lines, an immortalized cell or clonal population of immortalized cells, can be used, as well known in the art.

Antibodies that are specific for human tissue factor proteins or fragments thereof can be raised against an appropriate immunogenic antigen, such as isolated and/or tissue factor protein or a portion thereof (including synthetic molecules, such as synthetic peptides). Other specific or general mammalian antibodies can be similarly raised. Preparation of immunogenic antigens, and monoclonal antibody production can be performed using any suitable technique.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/O or the like, or heteromyelomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference. Antibody producing cells can also be obtained from the peripheral blood or, preferably the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; BioInvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350260(May 12, 1994); PCT/GB94/01422; PCT/GB94/02662; PCT/GB97/01835; (CAT/MRC); WO90/14443; WO90/14424; WO90/14430; PCT/US94/1234; W092/18619; WO96/07754; (Scripps); EP 614 989 (MorphoSys); WO95/16027 (BioInvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, now Applied Molecular Evolution (AME), each entirely incorporated herein by reference) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference) as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source which is non-human, e.g., but not limited to mouse, rat, rabbit, non-human primate or other mammal. These human amino acid residues are often referred to as "import" residues, which are typically taken from an "import" variable, constant or other domain of a known human sequence. Known human Ig sequences are disclosed, e.g., www.ncbi.nlm.nih.gov/entrez/query.fcgi; www.ncbi.nih.gov/igblast; www.atcc.org/phage/hdb.html; www.kabatdatabase.com/top.html; www.antibodyresource.com/onlinecomp.html; www.appliedbiosystems.com; www.biodesign.com; antibody.bath.ac.uk; http://www.unizh.ch/~antibody/; www.cryst.bbk.ac.uk/~ubcg07s; Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. Generally part or all of the non-human or human CDR sequences are maintained while the non-human sequences of the variable and constant regions are replaced with human or other amino acids. Antibodies can also optionally be humanized with retention of high affinity for the antigen and other favorable biological properties. To achieve this goal, humanized antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR (framework) residues can be selected and combined from the consensus and import sequences so that the desired antibody characteristic, such as increased affinity for the target antigen(s), is achieved. In general, the CDR residues are directly and most substantially involved in influencing antigen binding. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976, 862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

The tissue factor antibody can also be optionally generated by immunization of a transgenic animal (e.g., mouse, rat, hamster, non-human primate, and the like) capable of producing a repertoire of human antibodies, as described herein and/or as known in the art. Cells that produce a human tissue factor antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

To generate hybridomas producing human monoclonal antibodies to tissue factor, splenocytes and lymph node cells from immunized mice can be isolated and fused to an appropriate immortalized cell line, such as a mouse myeloma cell line. The resulting hybridomas can be screened for the production of antigen-specific antibodies.

Human antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VI, segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody; Prokaryotic expression of antibody genes has been reported to be ineffective for production of high yields of active antibody (Boss, M. A. and Wood, C. R. (I 985) Immunology Today 6:12-13).

Preferred mammalian host cells for expressing the recombinant antibodies of the invention include Chinese Hamster Ovary (CHO cells) (including dhfrCHO cells, described in Urlaub and Chasin, (1980) Proc. Natl. Acad. Sci. USA 77:42164220, used with a DHFR selectable marker, e.g., as described in R. J. Kaufman and P. A. Sharp (I 982) Mol. Biol. 159:601-62 1), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Screening antibodies for specific binding to similar proteins or fragments can also be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278. Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946, 778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge antibody Technologies; U.S. Pat. No. 5,750,373, assigned to Genentech, U.S. Pat. Nos. 5,618,920, 5,595,898, 5576195, 5698435, 5,693,493, 5,698,417, assigned to Xoma, Colligan, supra; Ausubel, supra; or Sambrook, supra, each of the above patents and publications entirely incorporated herein by reference.

Antibodies of the present invention can also be prepared using at least one tissue factor antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827, 690; 5,849,992; 4,873,316; 5,849,992; 5,994,616; 5,565,362; 5,304,489, and the like, each of which is entirely incorporated herein by reference.

Antibodies of the present invention can additionally be prepared using at least one tissue factor antibody encoding nucleic acid to provide transgenic plants and cultured plant cells (e.g., but not limited to tobacco, maize, and duckweed) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and reference cited therein. Thus, antibodies of the present invention can also be produced using transgenic plants, according to know methods. See also, e.g., Fischer et al., Biotechnol. Appl. Biochem. 30:99-108 (October 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. See, also generally for plant expression of antibodies, but not limited to, Each of the above references is entirely incorporated herein by reference.

2. Nucleic Acid Molecules

Using the information provided herein, such as the nucleotide sequences encoding at least 70-100% of the contiguous amino acids of at least one of SEQ ID NOS: 5 and 6, specified fragments, variants or consensus sequences thereof, or a deposited vector comprising at least one of these sequences, a nucleic acid molecule of the present invention encoding at least one anti-tissue factor antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising the coding sequence for, but not limited to, at least one specified portion of at least one CDR, as CDR1, CDR2 and/or CDR3 of at least one heavy chain (e.g., SEQ ID NOS: 7-9) or light chain (e.g., SEQ ID NOS:10-12); nucleic acid molecules comprising the coding sequence for an anti-tissue factor antibody or variable region (e.g., SEQ ID NOS: 2, 4, 5 and 6) including but not limited to SEQ ID Nos; 1 and 3; and nucleic acid molecules which comprise a nucleotide sequence substantially different from those described above but which, due to the degeneracy of the genetic code, still encode at least one anti-tissue factor antibody as described herein and/or as known in the art. Of course, the genetic code is well known in the art. Thus, it would be routine for one skilled in the art to generate such degenerate nucleic acid variants that code for specific anti-tissue factor antibodies of the present invention. See, e.g., Ausubel, et al., supra, and such nucleic acid variants are included in the present invention. Non-limiting examples of isolated nucleic acid molecules of the present inveniton include SEQ ID NOS: 5, 13-15, and 6, 16-18 corresponding to non-limiting examples of a nucleic acid encoding, respectively, HC variable region, HC CDR1, HC CDR2, HC CDR3, and LC variable region LC CDR1, LC CDR2, LC CDR3.

In another aspect, the invention provides isolated nucleic acid molecules encoding a(n) anti-tissue factor subunit antibody having an amino acid sequence as encoded by the nucleic acid contained in the plasmid designated clone p2401 and p2402.

As indicated herein, nucleic acid molecules of the present invention which comprise a nucleic acid encoding an anti-tissue factor antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

3. Polynucleotides Which Selectively Hybridize to a Polynucleotide as Described Herein The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

Preferably, the cDNA library comprises at least 80% full-length sequences, preferably at least 85% or 90% full-length sequences, and more preferably at least 95% full-length sequences. The cDNA libraries can be normalized to increase the representation of rare sequences. Low or moderate stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

Optionally, polynucleotides of this invention will encode at least a portion of an antibody encoded by the polynucleotides described herein. The polynucleotides of this invention embrace nucleic acid sequences that can be employed for selective hybridization to a polynucleotide encoding an antibody of the present invention. See, e.g., Ausubel, supra; Colligan, supra, each entirely incorporated herein by reference.

4. Construction of Nucleic Acids

The isolated nucleic acids of the present invention can be made using (a) recombinant methods, (b) synthetic techniques, (c) purification techniques, or combinations thereof, as well-known in the art.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra)

5. Recombinant Methods for Constructing Nucleic Acids

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra)

6. Nucleic Acid Screening and Isolation Methods

A cDNA or genomic library can be screened using a probe based upon the sequence of a polynucleotide of the present invention, such as those disclosed herein. Probes can be used to hybridize with genomic DNA or cDNA sequences to isolate homologous genes in the same or different organisms. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by one or more of temperature, ionic strength, pH and the presence of a partially denaturing solvent such as formamide. For example, the stringency of hybridization is conveniently varied by changing the polarity of the reactant solution through, for example, manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100%, or 70-100%, or any range or value therein. However, it should be understood that minor sequence variations in the probes and primers can be compensated for by reducing the stringency of the hybridization and/or wash medium.

Methods of amplification of RNA or DNA are well known in the art and can be used according to the present invention without undue experimentation, based on the teaching and guidance presented herein.

Known methods of DNA or RNA amplification include, but are not limited to, polymerase chain reaction (PCR) and related amplification processes (see, e.g., U.S. Pat. Nos. 4,683,195, 4,683,202, 4,800,159, 4,965,188, to Mullis, et al.; U.S. Pat. Nos. 4,795,699 and 4,921,794 to Tabor, et al; U.S. Pat. No. 5,142,033 to Innis; U.S. Pat. No. 5,122,464 to Wilson, et al.; U.S. Pat. No. 5,091,310 to Innis; U.S. Pat. No. 5,066,584 to Gyllensten, et al; U.S. Pat. No. 4,889,818 to Gelfand, et al; U.S. Pat. No. 4,994,370 to Silver, et al; U.S. Pat. No. 4,766,067 to Biswas; U.S. Pat. No. 4,656,134 to Ringold) and RNA mediated amplification that uses antisense RNA to the target sequence as a template for double-stranded DNA synthesis (U.S. Pat. No. 5,130,238 to Malek, et al, with the tradename NASBA), the entire contents of which references are incorporated herein by reference. (See, e.g., Ausubel, supra; or Sambrook, supra.)

For instance, polymerase chain reaction (PCR) technology can be used to amplify the sequences of polynucleotides of the present invention and related genes directly from genomic DNA or cDNA libraries. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

7. Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences. Such a method of constructing functional dsDNA molecules is taught in U.S. Pat. No. 6,521,427 and WO02081490.

8. Recombinant Expression Cassettes

The present invention further provides recombinant expression cassettes comprising a nucleic acid of the present invention. A nucleic acid sequence of the present invention, for example a cDNA or a genomic sequence encoding an antibody of the present invention, can be used to construct a recombinant expression cassette that can be introduced into at least one desired host cell. A recombinant expression cassette will typically comprise a polynucleotide of the present invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the present invention.

In some embodiments, isolated nucleic acids that serve as promoter, enhancer, or other elements can be introduced in the appropriate position (upstream, downstream or in intron) of a non-heterologous form of a polynucleotide of the present invention so as to up or down regulate expression of a polynucleotide of the present invention. For example, endogenous promoters can be altered in vivo or in vitro by mutation, deletion and/or substitution.

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (I 990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or P-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

9. Vectors and Host Cells

The present invention also relates to vectors that include isolated nucleic acid molecules of the present invention, host cells that are genetically engineered with the recombinant vectors, and the production of at least one anti-tissue factor antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827,739) resistance for eukaryotic cell culture, and tetracycline or ampicillin resistance genes for culturing in $E.$ $coli$ and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein of the present invention.

Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, PerC.6 cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin such as myeloma and lymphoma cells.

Expression vectors for these cells can include one or more of the following expression control sequences, such as, but not limited to an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art. Also, to avoid high surface expression of heavy chain molecules, it may be necessary to use an expression vector that eliminates transmembrane domain variant splices.

10. Purification of an Antibody

A tissue factor antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

11. Anti-Tissue Factor Antibodies of the Invention

Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of CNTO 860. The antibodies further can comprise the CDR2s of CNTO 860. The antibodies further can comprise the CDR1s of CNTO 860. Accordingly, the invention further provides anti-tissue factor antibodies comprising: (1) human heavy chain framework regions, a human heavy chain CDR1 region, a human heavy chain CDR2 region, and a human heavy chain CDR3 region, wherein the human heavy chain CDR3 region is as shown in SEQ ID NO: 9, and (2) human light chain framework regions, a human light chain CDR1 region, a human light chain CDR2 region, and a human light chain CDR3 region, wherein the human light chain CDR3 region is as shown in SEQ ID NO: 12, and (3) an Fc receptor binding domain; wherein the antibody binds human tissue factor and an Fc receptor on the surface of an effector cell. The antibody may further comprise the heavy chain CDR2 and/or the light chain CDR2 of CNTO 860, as shown in SEQ ID NO: 8 and/or 11, respectively. The antibody may further comprise the heavy chain CDR1 and/or the light chain CDR1 of CNTO 860, as shown in SEQ ID NO: 7 and/or 10, respectively.

In a preferred embodiment the three heavy chain CDRs and the three light chain CDRs of the anitbody or antigen-binding fragment have the amino acid sequence of the corresponding CDR of CNTO 860, as described herein. Such antibodies can be prepared by chemically joining together the various portions (e.g., CDRs and framework portions, FR1, FR2, FR3, and FR4) of the antibody using conventional techniques, by preparing and expressing a (i.e., one or more) nucleic acid molecule that encodes the antibody using conventional techniques of recombinant DNA technology or by using any other suitable method.

Preferably, the CDR1, 2, and/or 3 of the engineered antibodies described above comprise the exact amino acid sequence(s) as those of CNTO 860 disclosed herein. However, the ordinarily skilled artisan will appreciate that some deviation from the exact CDR sequences of CNTO 860 may be possible while still retaining the ability of the antibody to bind human tissue factor effectively (e.g., conservative substitutions). Accordingly, in another embodiment, the engineered antibody may be composed of one or more CDRs that are, for example, 90%, 95%, 98% or 99.5% identical to one or more CDRs of CNTO 860. In addition to binding tissue factor as well as an Fc receptor. Engineered antibodies such as those described above may be selected for their retention of other functional properties of antibodies of the invention, such as:

1). binding to live cells expressing human tissue factor; 2) binding to human tissue factor with a $K_D$ of $10^{-8}$ M or less (e.g., $10^{-9}$ M or $10^{-10}$ M or less); 3) binding to the unique epitope on tissue factor recognized by the TF8-5G9 antibody (to eliminate the possibility that monoclonal antibodies with complimentary activities when used in combination would compete for binding to the same epitope); 4) binding to an Fc receptor and is capable of eliciting effector functions including ADCC, complement activation, and C1q binding; and 4) inhibition of the growth of tumor cells in vivo.

Human monoclonal antibodies of the invention can be tested for binding to tissue factor by, for example, standard ELISA.

To determine if the selected human anti-tissue factor monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using tissue factor coated-ELISA plates. Biotinylated mAb binding can be detected with a strep-avidin-alkaline phosphatase probe. To determine the isotype of purified antibodies, isotype ELISAs can be performed. In order to demonstrate binding of monoclonal antibodies to live cells expressing the tissue factor, flow cytometry can be used. Anti-tissue factor human IgGs can be further tested for reactivity with tissue factor antigen by Western blotting.

An antibody of the invention can be of any class (IgG, IgA, IgM, etc.) that contains an Fc receptor binding domain and thus has the desired spectrum of effector functions conferred by that isotype and subclass and can comprise a kappa or lambda light chain. Quantifiable properties of antibody isotypes and subclasses thought to confer in vivo activities such as ADCC, CA, and opsinization are shown below and described in e.g. Janeway et al. eds., 2001. Immunobiology 5: The immune system in health an disease, Garland Publishing, NY, N.Y., USA. Chapters 4 and 9. In one embodiment, the antibody comprises an IgG heavy chain or defined fragment, for example, at least one of isotypes, IgG1, IgG2, or IgG3, preferably an IgG1 class. In another embodiment, the anti-human tissue factor antibody comprises an IgG1 heavy chain and a IgG1 light chain.

|  | IgG1 | IgG2 | IgG3 | IgG4 | IgM | IgA | IgE | IgD |
|---|---|---|---|---|---|---|---|---|
| Complement Activation | ++ | + | +++ | − | +++ | + | − | − |
| Phagocyte Binding | + | − | + | +/− | − | − | − | − |
| Neutralization | ++ | ++ | ++ | ++ | ++ | + | − | − |
| Opsinization | +++ | +/− | ++ | + | − | + | − | − |
| Sensitization for killing by NKs | ++ | − | ++ | − | − | − | − | − |
| Sensitization of Mast cells | + | − | + | − | − | − | − | +++ |
| Extra-vascular diffusion | +++ | +++ | +++ | +++ | +/− | ++ (sIgA) | − | + |

In another aspect of the invention, the structural features of an human anti-tissue factor antibodies of the invention, CNTO 860, are used to create structurally related human anti-tissue factor antibodies that retain the functional properties of the antibodies of the invention, i.e. the binding to human tissue factor and an Fc receptor.

The antibodies of the invention can bind human tissue factor with a wide range of affinities ($K_D$). In a preferred embodiment, at least one human mAb of the present invention can optionally bind human tissue factor with high affinity. For example, a human mAb can bind human tissue factor with a $K_D$ equal to or less than about $10_{-7}$ M, such as but not limited to, 0.1-9.9 (or any range or value therein)$\times 10^{-7}$, $10^{-8}$, $10^{-9}$, $10^{-11}$, $10^{-12}$, $10^{-13}$ M or any range or value therein.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer, such as the buffer described herein.

Preferably, the antibody or antigen-binding fragment of the invention binds human tissue factor and, thereby partially or substantially neutralizes at least one biological activity of the protein. An antibody, or specified portion or variant thereof, that partially or preferably substantially neutralizes at least one biological activity of at least one tissue factor protein or fragment can bind the protein or fragment and thereby inhibit activities mediated through the binding of tissue factor to its ligand or through other tissue factor-dependent or mediated mechanisms. As used herein, the term "neutralizing antibody" refers to an antibody that can inhibit a tissue factor-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-tissue factor antibody to inhibit a tissue factor-dependent activity is preferably assessed by at least one suitable tissue factor protein or receptor assay, as described herein and/or as known in the art.

In a specific embodiment, the anti-tissue factor antibody comprises an antibody having the amino acid sequence of the light chain of SEQ ID No. 4 and the amino acid sequence of the heavy chain of SEQ ID NO. 2.

An anti-tissue factor antibody of the present invention can include one or more amino acid substitutions, deletions or additions, either from natural mutations or human manipulation, as specified herein.Thus, the invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human tissue factor with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Of course, the number of amino acid substitutions a skilled artisan would make depends on many factors, including those described above. Generally speaking, the number of amino acid substitutions, insertions or deletions for any given anti-tissue factor antibody will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-tissue factor antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one tissue factor neutralizing activity. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Anti-tissue factor antibodies of the present invention can include, but are not limited to, at least one portion, sequence or combination selected from 5 to all of the contiguous amino acids of at least one of SEQ ID NOS: 2 and 4.

A(n) anti-tissue factor subunit antibody can further optionally comprise a polypeptide of at least one of 70-100% of the contiguous amino acids of at least one of SEQ ID NOS: 5 and 6 and an Fc binding portion.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS: 2 and 4. For example, the amino acid sequence of a light chain variable region can be compared with the sequence of SEQ ID NO: 6, or the amino acid sequence of a heavy chain CDR3 can be compared with SEQ ID NO: 9. Preferably, 70-100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOS: 5 and 6. The antibodies of the present invention, or specified variants thereof, can comprise any number of contiguous amino acid residues from an antibody of the present invention, wherein that number is selected from the group of integers consisting of from 10-100% of the number of contiguous residues in an anti-tissue factor antibody. Optionally, this subsequence of contiguous amino acids is at least about 10, 20, 30, 40, 50, 60, 70, 80, 90, 100, 110, 120 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-100% of that of the native (non-synthetic), endogenous or related and known antibody. Methods of assaying and quantifying measures of enzymatic activity and substrate specificity, are well known to those of skill in the art.

In another aspect, the invention relates to antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-$\Delta$9-octadecanoate ($C_{18}$, oleate), all cis-$\Delta$5,8,11,14-eicosatetraenoate ($C_{20}$, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

12. Anti-Tissue Factor Antibody Compositions

The present invention also provides at least one anti-tissue factor antibody composition comprising at least one tissue factor antibody as described herein and/or as known in the art that are provided in a non-naturally occurring composition, mixture or form. Anti-tissue factor antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990. Pharmaceutically acceptable carriers can be routinely selected that are suitable for the mode of administration, solubility and/or stability of the anti-tissue factor antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-tissue factor antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, anti-tissue factor subunit antibody compositions of the invention can include polymeric excipients/additives such as polyvinylpyrrolidones, ficolls (a polymeric sugar), dextrates (e.g., cyclodextrins, such as 2-hydroxypropyl-α-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti tissue factor antibody, portion or variant compositions according to the invention are known in the art, e.g., as listed in "Remington: The Science & Practice of Pharmacy", 19th ed., Williams & Williams, (1995), and in the "Physician's Desk Reference", 52nd ed., Medical Economics, Montvale, N.J. (1998), the disclosures of which are entirely incorporated herein by reference.

Preferrred carrier or excipient materials are carbohydrates (e.g., saccharides and alditols) and buffers (e.g., citrate) or polymeric agents.

Anti-tissue factor antibody compositions of the present invention can optionally further comprise at least one additional agent selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteroid, (dexamethasone), an anabolic steroid (testosterone), a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin (rituximab), an immunosuppressive (e.g., basiliximab, cyclosporine, daclizumab), a growth hormone, a hormone antagonist, a reproductive hormone antagonist (flutamide, nilutamide), a hormone release modulator (leuprolide, goserelin), a hormone replacement drug, an estrogen receptor modulator (tamoxifen), a retinoid (tretinoin), a topoisomerase inhibitor (etoposide, irinotecan), a cytoxin (doxorubicin, dacarbazine), a mydriatic, a cycloplegic, an alkylating agent (carboplatin), a nitrogen mustard (melphalen, chlorabucil), a nitrosourea (carmustine, estramustine) an antimetabolite (methotrexate, cytarabine, fluorouracil), a mitotic inhibitor (vincristine, taxol), a radiopharmaceutical (Iodine131-tositumomab), a radiosensitizer (misonidazole, tirapazamine) an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine (interferon alpha-2, IL2) or a cytokine antagonist (infliximab). Non-limiting examples of such cytokines include, but are not limted to, any of IL-1 to IL-23, IL-6, anti-tumor antibodies, chemotherapeutic agents or radiation therapies. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

The method may be carried out by combining the TF antagonists of the invention with one or more other agents having anti-tumor effect or a dissimilar mechanism of inhibiting in vivo tumor growth, including, but not limited to chemotherapeutic agents.

Further, the TF antibody can be combined with one or more anti-angiogenic agents. Angiogenesis is characterized by the invasion, migration and proliferation of smooth muscle and endothelial cells. The αvβ3 integrin (also known as the vitronectin receptor) is known to play a role in various conditions or disease states including tumor metastasis, solid tumor growth (neoplasia), osteoporosis, Paget's disease, humoral hypercalcemia of malignancy, angiogenesis, including tumor angiogenesis, retinopathy, including macular degeneration, arthritis, including rheumatoid arthritis, periodontal disease, psoriasis and smooth muscle cell migration (e.g. restenosis).

The adhesion receptor integrin αvβ3 binds vitronectin, fibrinogen, von Willebrand Factor, laminin, thrombospondin, and other like ligands. It was identified as a marker of angiogenic blood vessels in chick and man and plays a critical role in angiogenesis or neovascularization. Antagonists of αvβ3 inhibit this process by selectively promoting apoptosis of cells in neovasculature. Therefore, αvβ3 antagonists would be useful therapeutic targets for treating such conditions associated with neovascularization (Brooks et al., Science, Vol. 264, (1994), 569-571). Additionally, tumor cell invasion occurs by a three step process: 1) tumor cell attachment to extracellular matrix; 2) proteolytic dissolution of the matrix; and 3) movement of the cells through the dissolved barrier. This process can occur repeatedly and can result in metastases at sites distant from the original tumor. The αvβ3 integrin has been shown to play a role in tumor cell invasion as well as angiogenesis.

As the antagonists of αvβ3 and neutralizing anti-TF antibodies both target tumors but act through different mechanisms, the combination of anti-integrin antibodies with anti-TF antibodies should result in a particularly potent and effective combination therapy with little normal tissue toxicity. Thus, in one embodiment of the present invention, there is provided a method of inhibiting the growth of tumors which comprises administering a combination of an integrin antagonist and an anti-TF antibody in a patient in need of such treatment. Other antibodies which selectively bind integrins or integrin subunits, especially those that bind the alphaV subunit, are disclosed in U.S. Pat. Nos. 5,985,278 and 6,160,099. Mabs that inhibit binding of alphaVbeta3 to its natural ligands containing the tripeptide argininyl-glycyl-aspartate (RGD) are disclosed in U.S. Pat. No. 5,766,591 and WO0078815. Other antibodies that prevent alphaV-subunit containing integrins from binding to vitronection, fibronectin, or other ligands have similar utility in preventing angiogenesis. Such antibodies include the antibody known at GEN 095 or CNTO 95 and described in applicants co-pending application published as WO02012501.

In accordance with the invention, other known anti-angiogenesis agents such as thalidomide may also be employed in combination with an anti-tissue factor antibody.

The invention also pertains to immunoconjugates comprising the antibody described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate).

Such anti-cancer can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), *Streptococcal* enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii*, and *Shigella sonnei*), *Salmonella* species (e.g., *Salmonella typhi, Salmonella cholera-suis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa*, and *Streptococci*. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., The Merck Manual, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Chemotherapeutic agents useful in the generation of such immunoconjugates have been described above.

A variety of radionuclides are available for the production of radioconjugated anti-TF antibodies.

Conjugates of the antibody and cytotoxic agent are made using a variety of bifunctional protein coupling agents such as N-succinimidyl(2-pyridyldithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bisdiazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon labeled I-isothiocyanatobenzyl methyldiethylene triaminepentaacetic acid (MX-DTPA) is an exemplary chelating agent for conjugation of radionucleotide to the antibody. See WO94/11026.

The anti-Tissue factor antibodies disclosed herein may also be formulated as immunoliposomes. Liposomes containing the antibody are prepared by methods known in the art, such as described in Epstein et al., Proc. Natl. Acad. Sci. USA 82:3688 (1985); Hwang et al., Proc. Natl Acad. Sci. USA 77:4030 (1980 Particularly useful liposornes can be generated by the reverse phase evaporation method with a lipid composition comprising phosphatidylcholine, cholesterol and PEG-derivatized phosphatidylethanolarnine (PEG-PE). Liposornes are extruded through filters of defined pore size to yield liposornes with the desired diameter. Fab' fragments of the antibody of the present invention can be conjugated to the liposornes as described in Mar-tin et al., J. Biol. Chem. 257: 286-288 (1982) via a disulfide interchange reaction. A chemotherapeutic agent (such as Doxorubicin) is optionally contained within the liposorne. See Gabizon et al., J National Cancer Inst. 81(19):1484 (1989).

14. Formulations

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one anti-tissue factor antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1., 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one anti-tissue factor subunit antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one anti-tissue factor antibody, and a second vial comprising an aqueous diluent of prescribed buffer or preservative, wherein said packaging material comprises a label that instructs a patient to reconstitute the at least one anti-tissue factor antibody in the aqueous diluent to form a solution that can be held over a period of twenty-four hours or greater.

The at least one tissue factor antibody used in accordance with the present invention can be produced by recombinant means, including from mammalian cell or transgenic preparations, or can be purified from other biological sources, as described herein or as known in the art.

The range of tissue factor subunit antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof.

The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one tissue factor antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one tissue factor antibody and preservative in an aqueous diluent is carried out using conventional dissolution and mixing procedures. To prepare a suitable formulation, for example, a measured amount of at least one tissue factor antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized tissue factor antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of tissue factor antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one tissue factor antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one anti-tissue factor antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen (Franklin Lakes, N.J., www.bectondickenson-.com), Disetronic (Burgdorf, Switzerland, www.disetronic-.com; Bioject, Portland, Oreg. (www.bioject.com); National Medical Products, Weston Medical (Peterborough, UK, www.weston-medical.com), Medi-Ject Corp (Minneapolis, Minn., www.mediject.com). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one tissue factor antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one anti-tissue factor antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized tissue factor antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

Ttissue factor antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

15. Therapeutic Applications

The TF antagonists of the invention are useful in inhibiting and preventing tumor growth. A number of pathologies involving various forms of solid primary tumors are improved by treatment with TF antagonists in the method of the present invention.

Tumors

Both benign and malignant tumors, including various cancers such as, cervical, anal and oral cancers, stomach, colon, bladder, rectal, liver, pancreatic, lung, breast, cervix uteri, corpus uteri, ovary, prostate, testis, renal, brain/cns (e.g., gliomas), head and neck, eye or ocular, throat, skin melanoma, acute lymphocytic leukemia, acute myelogenous leukemia, Ewing's Sarcoma, Kaposi's Sarcoma, basal cell carinoma and squamous cell carcinoma, small cell lung cancer, choriocarcinoma, rhabdomyosarcoma, angiosarcoma, hemangioendothelioma, Wilms Tumor, neuroblastoma, mouth/pharynx, esophageal, larynx, kidney and lymphoma, among others may be treated using anti-TF antibodies of the present invention.

Thus, the present invention provides a method for modulating or treating at least one malignant disease in a cell, tissue, organ, animal or patient, including, but not limited to, at least one of: breast carcinoma, colorectal carcinoma, renal cell carcinoma, pancreatic carcinoma, prostatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, and the like. Such a method can optionally be used in combination with, by administering before, concurrently or after administration of such TF antagonist, radiation therapy, an anti-angiogenic agent, a chemotherapeutic agent, a farnesyl transferase inhibitor, a protesome inhibitor or the like.

Any method of the present invention can comprise administering an effective amount of a composition or pharmaceutical composition comprising at least one The TF antagonists of the invention are useful in inhibiting and preventing tumor growth. A number of pathologies involving various forms of solid primary tumors are improved by treatment with TF antagonists in the method of the present invention.

Particular combinations for treatment of neoplastic diseases comprise co-administration or combination therapy by administering, before concurrently, and/or after, an antineplastic agent such as an alkylating agent, a nitrogen mustard, a nitrosurea, an antibiotic, an anti-metabolite, a hormonal agonist or antagonist, an immunomodulator, and the like. For use in metastatic melanoma and other neoplastic diseases,a preferred combination is to co-administer the antibody with dacarbazine, interferon alpha, interleukin-2, temozolomide, cisplatin, vinblastine, Imatinib Mesylate, carmustine, paclitaxel and the like. For metastatic melanoma, dacarbazine is preferred.

Therapeutic Treatments

Typically, treatment of pathologic conditions is effected by administering an effective amount or dosage of at least one anti-tissue factor antibody composition that total, on average, a range from at least about 0.01 to 500 milligrams of at least one tissue factor antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 μg/ml serum concentration per single or multiple adminstration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and non-aqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

While having described the invention in general terms, the embodiments of the invention will be further disclosed in the following examples.

EXAMPLE 1

Preparation of IgG1 Tissue Factor Antibody (CNTO860)

For oncology indications it is generally preferable to use a human IgG1 isotype subclass antibody, rather than IgG4, to maximize ADCC and CDC mechanisms of tumor cell killing. The IgG1 version of CNTO 859 is disclosed here and is designated CNTO 860.

An additional property of human IgG4 isotype antibodies is their tendency to lose their inter-chain disulfide bonds via isomerization with intra-chain residues, allowing the two antigen binding halves of the molecule to dissociate from each other and associate with unrelated IgG4 half molecules. Monovalency is undesirable for a therapeutic molecule as the avidity of binding of the antibody for its target is reduced. Therefore, a Ser to Pro mutation in the hinge region at aa residue 228 as shown in SEQ ID NO: 2 of the antibody prevents this phenomenon.

Preparation of CNTO860 Heavy and Light Chain Expression Plasmids

The CNTO860 heavy chain expression plasmid was prepared by polymerase chain reaction amplification of the CNTO859 heavy chain variable region from plasmid pEe6TF8HCCDR20 using oligos HuG1 CNTO859HC forward (SEQ ID NO: 19) and HuG1 CNTO859HC reverse (SEQ ID NO: 20) (Table 1). The resulting PCR product was digested with Nco I and Hind III, and cloned into the same restriction sites of p1340. The resulting vector contained the CNTO859 HC variable region downstream of a part of a mouse immunoglobulin promoter. This vector was digested with Xba I and cloned into vector p730. The resulting expression plasmid, p2401, contained an intact mouse immunoglobulin promoter, the CNTO859 HC variable region, the exons for a human G1 constant region, and the gene for *E.coli* guanine phosphoribosyl transferase. The HC variable region of p2401 was sequenced, and found to contain no PCR or cloning errors.

The CNTO860 light chain expression plasmid was prepared by polymerase chain reaction amplification of the CNTO859 light chain variable region from plasmid pEe12TF8LCDR3 using oligos HuK CNTO859 LC forward (SEQ ID NO: 21) and HuKCNTO859 LC reverse (SEQ ID NO: 22) (Table 1). The resulting PCR product was digested with Bgl II and Sal I and cloned into the same restriction sites of p2287. The resulting vector contained the CNTO859 LC variable region downstream of a mouse kappa promoter. This vector was digested with Hind III and cloned into vector p95. The resulting expression plasmid, p2402, contained a mouse kappa promoter, the CNTO859 LC variable region, a human kappa light chain constant region, and the gene for *E. coli* guanine phosphoribosyl transferase. The LC variable region of p2402 was sequenced, and found to contain no PCR or cloning errors.

TABLE 1

| PCR Oligonucleotide | Sequence |
|---|---|
| HuG1 CNTO859HC forward | 5'-GCC ACC ATG GAA TGG-3'<br>           Nco I |
| HuG1 CNTO859HC reverse | 3'-GGT CAG TGG CAC TCG AGT CCA TTC AAG ATC TTC GAA CCG-5'<br>           Xba I   Hind III |
| CNTO859 LC forward | 5'-GTG AGA TCT GAA ATA CAT CAG<br>         Bgl II<br>ATC ACC ATG GGT GTG CCA ACT CAG-3' |
| HuKCNTO859 LC reverse | 3'-CCT TGT TTT GAT CTC TAG TGTGCA TTC ATT CGA ACA GCT GAG A-5'<br>        Hind III   Sal I |

The CNTO860 expression plasmids p2401 and p2402, were transfected into NS0 cells for stable expression.

EXAMPLE 2

Effect of Anti-TF Antibody on Human Breast Carcinoma in an Orthotopic Xenograft Model In this example, an orthotopic tumor growth model using the human breast carcinoma cell line, MDA MB 231, injected into the mammary fat pad of SCID/Beige mice was used to test the anti-tumor effect of CNTO 859. In addition, the effect of variations on the structure of anti-tissue factor antibody were compared: one differing in human IgG subclass identity CNTO 859 (IgG4) and CNTO 860 (IgG1); and modification of the FcR binding region CNTO 859 designated CNTO 859 ala/ala where residues 235 and 23 are replaced with alanine residues. Substitution of amino acids Phe234 and Leu235 with ala residues in an IgG4 has been shown to greatly reduce Fc receptor binding, a prerequisite for ADCC activity (Xu D, et al. (2000) Cell Immunol 200:16-26).

Materials and Methods Four week-old female SCID/Beige mice (C.B.-17/IcrCrl-scid-bgBR) from Charles River Laboratories were obtained and acclimated for 10-14 days prior to experimentation. All animal studies were carried out in accordance to the National Institutes of Health Guide for the Care and Use of Laboratory Animals.

The human breast carcinoma cell line MDA MB 231 was obtained from the cell repository at Centocor and have been deemed sterile and mycoplasma-free. Cells were cultured in DMEM media supplemented with 10% FBS and 1% LNN at 37° C., 5% $CO_2$. Cells were harvested at log phase growth with trypsin-EDTA and resuspended at $5 \times 10^7$ cells/mL in serum-free DMEM and were implanted into the (Rt inguinal #2/3) mammary fat pad in a volume of 50 uL.

Test and Control Antibodies were as follows: CNTO 859, 3.75 mg/mL stock concentration; CNTO 859, 10.29 mg/mL stock; CNTO 860, 2.4 mg/mL stock; CNTO 859 Ala/Ala, C1081, 1 mg/mL stock; Human Ig, ZLB Bioplasma AG, Berne Switzerland, 30 mg/mL stock concentration.

Antibodies were supplied at appropriate concentrations in PBS. All control and test articles have been endotoxin tested to be <1 EU/mg and will be administered intravenously.

Animals were randomized 7-8 mice/group. On day 0, $2.5 \times 10^6$ MDA MB 231 cells were injected into the mammary fat pad of the animals in a volume of 50 uLs using a 30 g needle. Intravenous antibody therapy commenced on day 3. Dosing regimens and concentrations for each of the three studies are detailed in Tables 2, 3 and 4, respectively.

TABLE 2

| Group | Mice/Group | Cells | Treatment | Weekly ×8 |
|---|---|---|---|---|
| 1 | 8 | MDA MB 231 | PBS | 200 uL |
| 2 | 8 | MDA MB 231 | PBS | 200 uL |
| 3 | 8 | MDA MB 231 | CNTO 859 | 20 mg/kg |
| 4 | 8 | MDA MB 231 | Hu IgG | 20 mg/kg |

TABLE 3

| Group | Mice/Group | Cells | Treatment | Weekly ×8 |
|---|---|---|---|---|
| 1 | 8 | MDA MB 231 | PBS | 200 uL |
| 2 | 8 | MDA MB 231 | Hu IgG | 20 mg/kg |
| 3 | 8 | MDA MB 231 | CNTO 859 | 0.1 mg/kg |
| 4 | 8 | MDA MB 231 | CNTO 859 | 1.0 mg/kg |
| 5 | 8 | MDA MB 231 | CNTO 859 | 5 mg/kg |
| 6 | 8 | MDA MB 231 | CNTO 859 | 10 mg/kg |
| 7 | 8 | MDA MB 231 | CNTO 859 | 20 mg/kg |

TABLE 4

| Group | Mice/Group | Cells | Treatment | Weekly ×8 |
|---|---|---|---|---|
| 1 | 7 | MDA MB 231 | PBS | 200 uL |
| 2 | 7 | MDA MB 231 | Hu IgG | 1 mg/kg |
| 3 | 7 | MDA MB 231 | CNTO 859 | 1 mg/kg |
| 4 | 7 | MDA MB 231 | CNTO 859 | 0.1 mg/kg |
| 5 | 7 | MDA MB 231 | CNTO 859 | 0.01 mg/kg |
| 6 | 7 | MDA MB 231 | CNTO 860 | 1 mg/kg |
| 7 | 7 | MDA MB 231 | CNTO 860 | 0.1 mg/kg |
| 8 | 7 | MDA MB 231 | CNTO 860 | 0.01 mg/kg |
| 9 | 7 | MDA MB 231 | CNTO 859 ala/ala | 1 mg/kg |

The mice were weighed and tumor volumes were recorded once weekly for a period of 8-9 weeks. Tumor volumes were calculated as $(L \times W^2)/2$. The study terminated approximately eight to nine weeks after tumor cell inoculation. In the case that any animal experiences rapid weight loss, respiratory difficulty or becomes moribund prior to the termination point, that animal was euthanized by the Study Coordinator. Animals were euthanized via $CO_2$ asphyxiation and then weighed. Lungs and axillary lymph nodes were surgically removed, rinsed in cold PBS, blotted, weighed and immediately fixed in Bouin's solution. Primary tumors were resected, weighed and then fixed in BZT solution for histological analysis.

Figure 3:
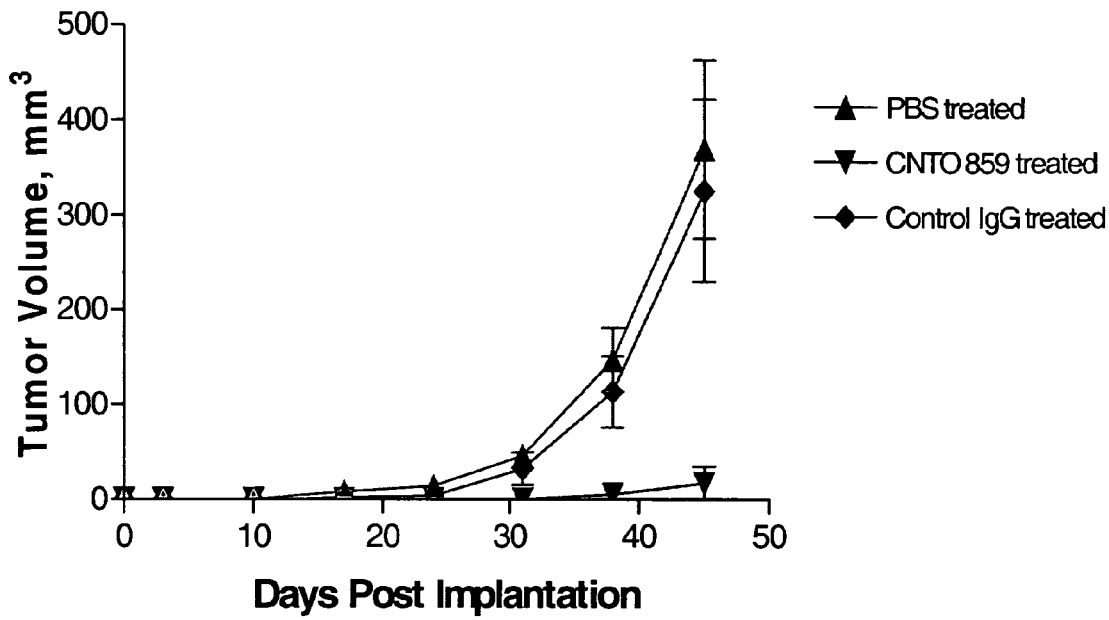
FIG. 3 is a graph showing the change in tumor volumes from either control animals, animals treated with either PBS or control human Ig and animals treated with CNTO 859.
Figure 4:
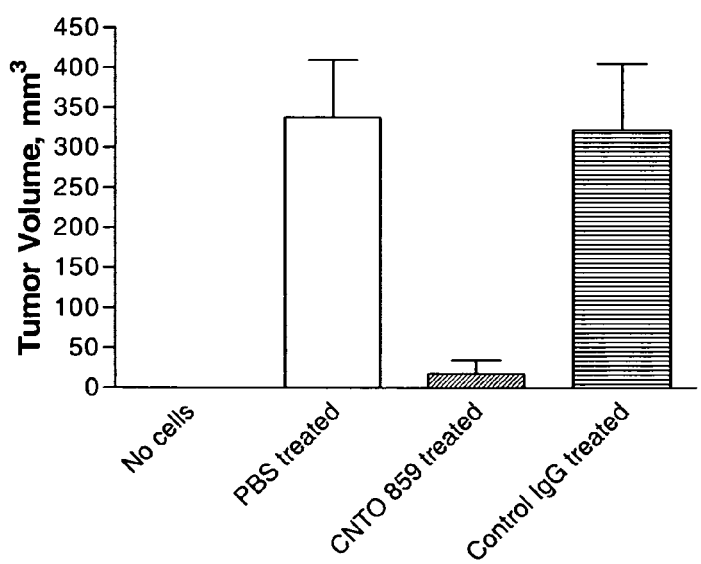
FIG. 4 is a bar graph representing the mean and standard deviation of the final tumor volumes from either control animals, animals treated with either PBS or control IgG and animals treated with CNTO 859.

Primary Anti-Tumor Effect (Study 1) Tumor volumes were monitored and recorded once weekly during the study. At termination, primary tumors were surgically resected from $CO_2$ euthanized SCID/Beige mice and weighed. Tumor volumes and final mass were plotted over time (FIGS. 3 and 4). Tumor growth was inhibited by over 95% when animals were treated with CNTO 859 at 20 mg/kg×8 relative to either the PBS or control Ig treated animals (p=0.0039 and p=0.0126, two-tailed parametric t test, n=8).

Figure 5:
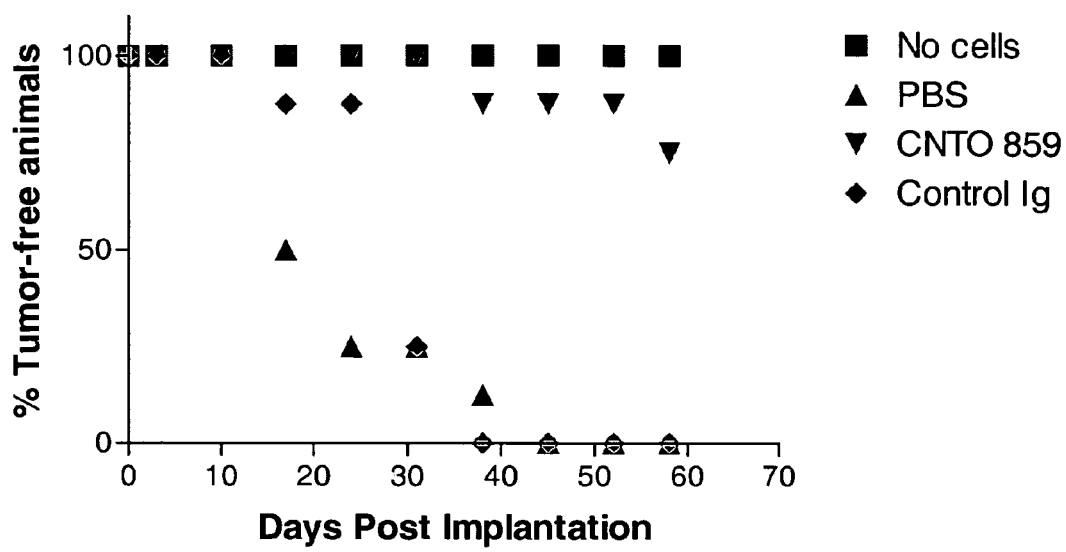
FIG. 5 shows the tumor incidence rate in animals treated with either PBS, control Ig or CNTO 859 beginning on the same day as the tumor cells were implanted.

Effect on Tumor Incidence. CNTO 859 also caused a marked difference in tumor incidence in treated animals as measured by the time post-tumor cell injection for a measurable mass to develop in the animals. In the Study 1, measurable tumors appeared in PBS or control human Ig treated animals beginning on day 17. In the mice treated with CNTO 859, cells were able to adhere and seed in the mammary fat pad as observed by the palpation of a nodule at the injection site but were too small to measure until approximately day 38, when one tumor was of measurable size. FIG. 5 shows the tumor incidence rate in animals treated with either PBS, control Ig or CNTO 859. Thus, these results using an orthotopic MDA MB 231 tumor growth model, indicate that CNTO 859 is a highly effective inhibitor of tumor incidence, growth and progression. Compared with a vehicle control or Ig control, CNTO 859 reduced tumor incidence by 87.5% (p=0.0017 vs PBS and p=0.0086 vs control human Ig, two-tailed parametric t test, n=8).

Figure 6:
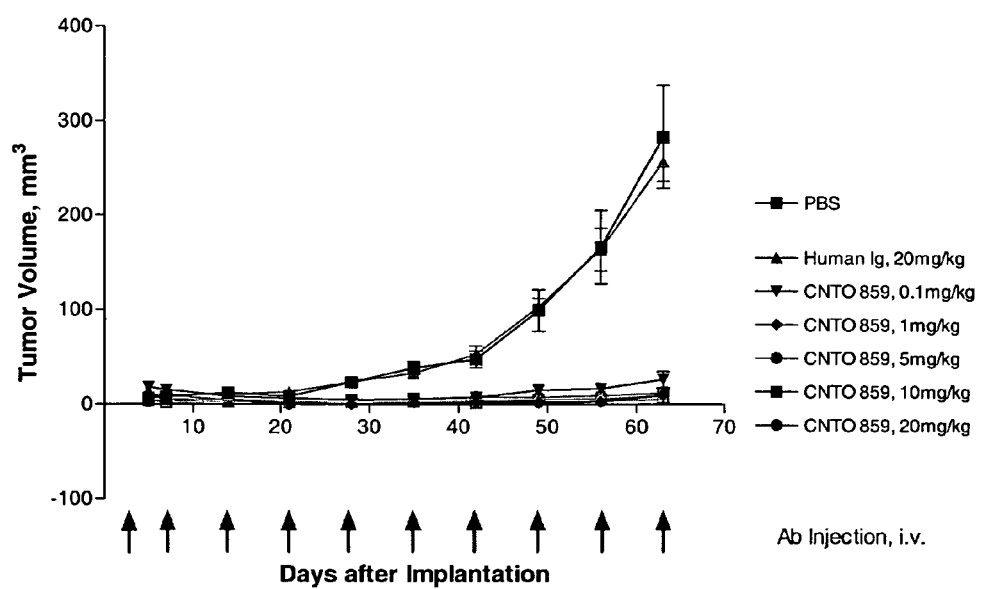
Figure 7:
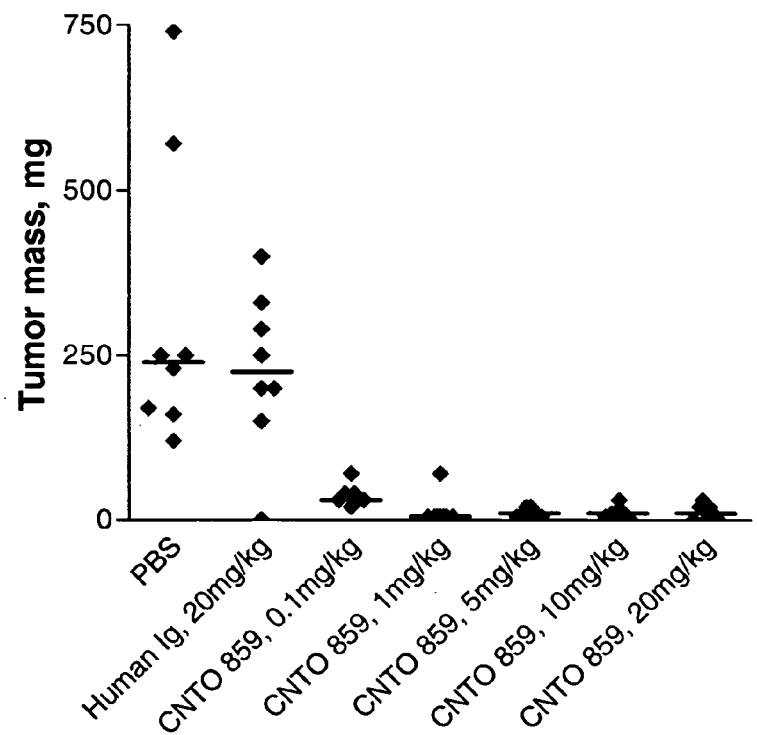
FIG. 7 is a scatter plot showing the distribution of final tumor volumes from animals treated with either PBS, control human Ig or various dosages of CNTO 859 (0.1, 1, 5, 10 and 20 mg/kg).
Figure 8:
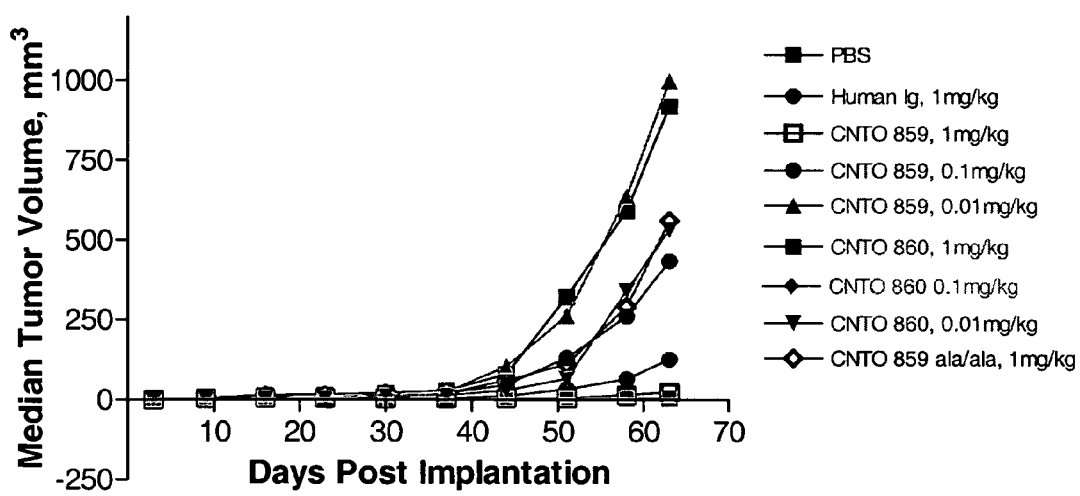
FIG. 8 is graph of tumor volumes over time for an experiment using human breast cancer cells MDA MB 231 xenografts implanted in mice orthotopically (in mammary tissue) and where the mice were treated with either PBS, control human Ig, CNTO 859 Ala/Ala or various dosages (0.01, 0.1 and 1 mg/kg) of CNTO 859 and CNTO 860.
Figure 9:
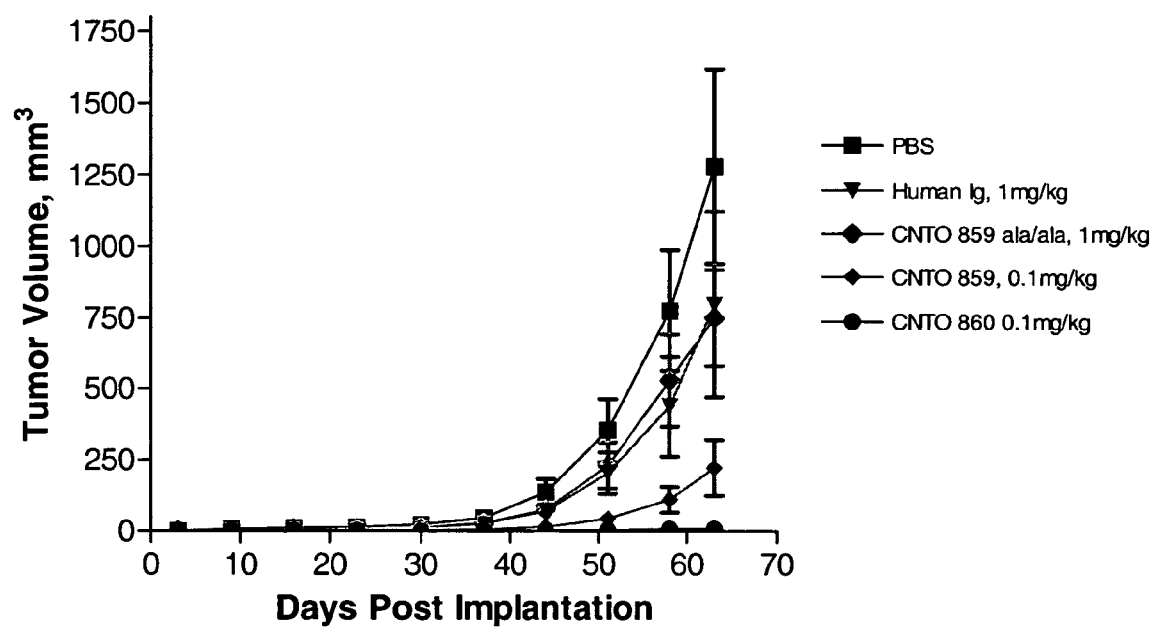
FIG. 9 shows means and standard deviation of four of the groups from the same experiment shown in FIG. 8, showing only the controls and CNTO 859 and CNTO 860 at 0.1 mg/kg.
Figure 10:
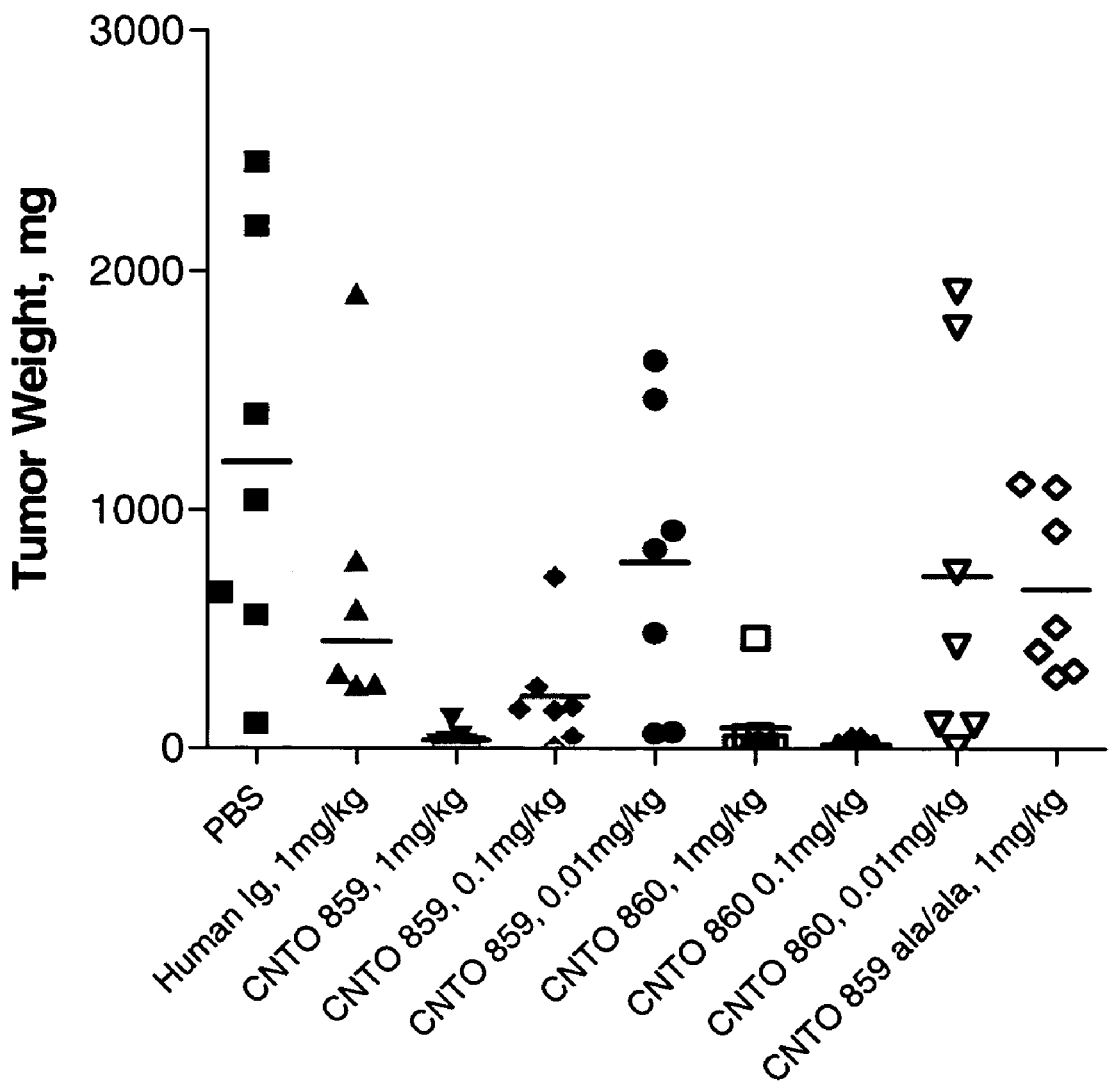
FIG. 10 is a graphical representation of each of the individual final tumor volumes and means from each group in the same experiment as FIG. 8.

Dosing Ranging Study (Study 2) the effect of dose was examined. CNTO 859 inhibited tumor growth at doses as low as 0.1 mg/kg, given once weekly. There was a significant reduction in tumor progression as measured by tumor volume change (FIG. 6) and individual final tumor weights (FIG. 7) in animals treated with either 0.1, 1, 5, 10 or 20 mg/kg of CNTO 859 compared to PBS and Human Ig control groups.

Figure 11:
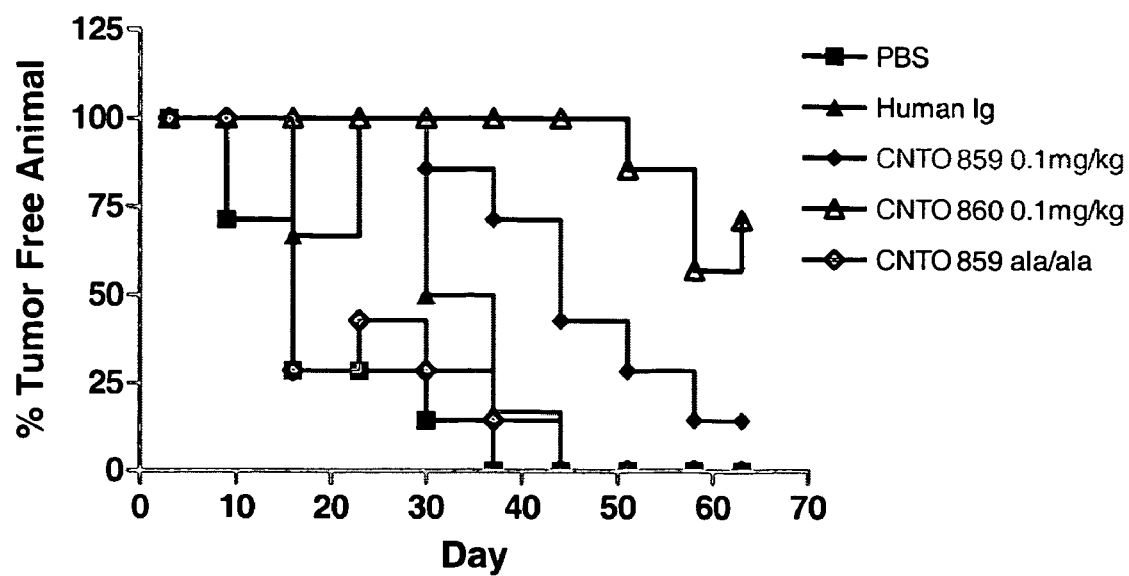
FIG. 11. shows the tumor incidence data from the same experiment as in FIG. 8.

Effect of Isotype (Study 3) In a comparison study between CNTO 859 and CNTO 860 at three concentrations, it was shown that the IgG1 version of the anti-tissue factor antibody was superior in preventing not only tumor growth, but also tumor incidence (FIGS. 8-11). Tumor volumes from each of the respective groups are shown as median tumor weight in the group over time (FIG. 8), mean and standard deviation of selected groups (FIG. 9), as individual final tumor weights for all animals in the study (FIG. 10), and tumor free survival rate/incidence rate (FIG. 11).

Summary CNTO 859 and two variants were compared for efficacy in preventing tumor growth and progression in a series of experiments using this xenograft model. In the first study, CNTO 859 was highly efficacious in preventing tumor growth when given once weekly starting on day 3 post-tumor implantation at a concentration of 20 mg/kg, resulting in a 95% growth inhibition rate compared to either the PBS or control Ig treatment groups (p=0.0039 and p=0.0126, respectively). We also observed an 87.5% reduction in tumor incidence in animal treated with CNTO 859 compared to either the PBS or control Ig treatment groups (p=0.0017 and p=0.0086, respectively).

In Study 2, CNTO 859 was administered at a series of dosages ranging from 0.1 mg/kg to 20 mg/kg once weekly. Results show that anti-TF monoclonal antibody therapy with CNTO 859 was highly efficacious in slowing tumor progression, even at a very low dose of 0.1 mg/kg, resulting in over 90% tumor inhibition compared to either the PBS or control Ig treatment groups (p=0.0012 and p=0.0106, respectively, Wilcoxon two-sample test using t-distribution). Dosages of 1, 5, 10 and 20 mg/kg significantly inhibited tumor growth by over 95%.

In Study 3, the efficacy of CNTO 859 was evaluated against CNTO 860, an IgG1 version of CNTO 859, and the ADCC minimized version, CNTO 859 ala/ala. Doses of 0.01 mg/kg of either the IgG4 or IgG1 therapeutic antibody was no different than PBS, Human Ig control or CNTO 859 Ala/Ala. In contrast, a dose of 1 mg/kg of either CNTO 859 or CNTO 860 was able to inhibit tumor growth by over 95%. Interestingly, at the 0.1 mg/kg dose level, the effect CNTO 859 versus CNTO 860 is distinguished as CNTO 860 inhibited tumor growth by over 95% even at this low dose while CNTO 859 treated tumors were showing signs of escape from therapy, resulting in only ~85% inhibition. In addition, CNTO 860 was more effective than CNTO 859 at slowing tumor progression when used at 0.1 mg/kg, presumably due to additional ADCC activity.

In Study 3, evaluation of the incidence and onset of tumors for CNTO 859 and CNTO 860 at the dose level of 0.1 mg/kg, CNTO 860 was able to delay initial tumor onset to 54 days and as compared to compared to the PBS and Human Ig control groups in which tumors developed by days 10 or 17 (by 44 and 37 days) while CNTO 859 was able to delay initial tumor onset by 23 and 16 days. Furthermore, by the end of the study, over 70% of the animals were tumor-free in the CNTO 860 group compared to only 15% in the CNTO 859 group. All animals in the PBS, Human Ig and CNTO 859 ala/ala groups had tumors by day 44 (FIG. 11).

EXAMPLE 3

Activity Profiles

Native antigen binding affinity and measures of coagulation inhibition were performed using CNTO859 and CNTO860.

Flow Cytometric Analysis. MDA-MB-231 cells ($3 \times 10^5$) were stained with log-fold titrated amounts of CNTO 859 in serum-free RPMI media for 1 hr on ice. After multiple washes, bound CNTO 859 was detected with a PE conjugated goat-anti human Ig (10 ug/mL) for 30 min on ice. Cells were washed and fixed in 1% paraformaldehyde and total fluorescence was detected on a FACS Calibur.

Factor X Activation Assay. Human brain extract and FVIIa was added for 10 min to allow FVIIa to bind to tissue factor. At t=0, increasing concentrations of FX with or without CNTO 859 or CNTO 860 was added. The reactions were quenched with EDTA at various times. S2765, a substrate of FXa, was added and the conversion of S2765 substrate to a chromogenic product was monitored at 405 nm every 12 s for 10 min. The amount of FXa produced in the reaction was determined using a standard curve that measures S2765 conversion at known FXa concentrations. The amount of FXa produced was plotted as a function of time in order to determine the rate of FXa production. The rate of FXa production was plotted as a function of FX concentration. FVIIa, FX, and FXa were obtained through Haematologic Technologies (Essex Junction, Vt.). S2765 substrate was purchased from DiaPharma (West Chester, Ohio).

Coagulation Assay. Titrated amounts of CNTO 859 was added to an equal volume of citrated human plasma. Wells were mixed and transferred to a 96-well plate containing Simplastin supplemented with $CaCl_2$. Plates were read immediately in a EIA plate reader at 450 nM every 15 sec for 2 hrs. Clotting time (time to reach the max O.D.) was plotted against antibody concentration.

Figure 12:
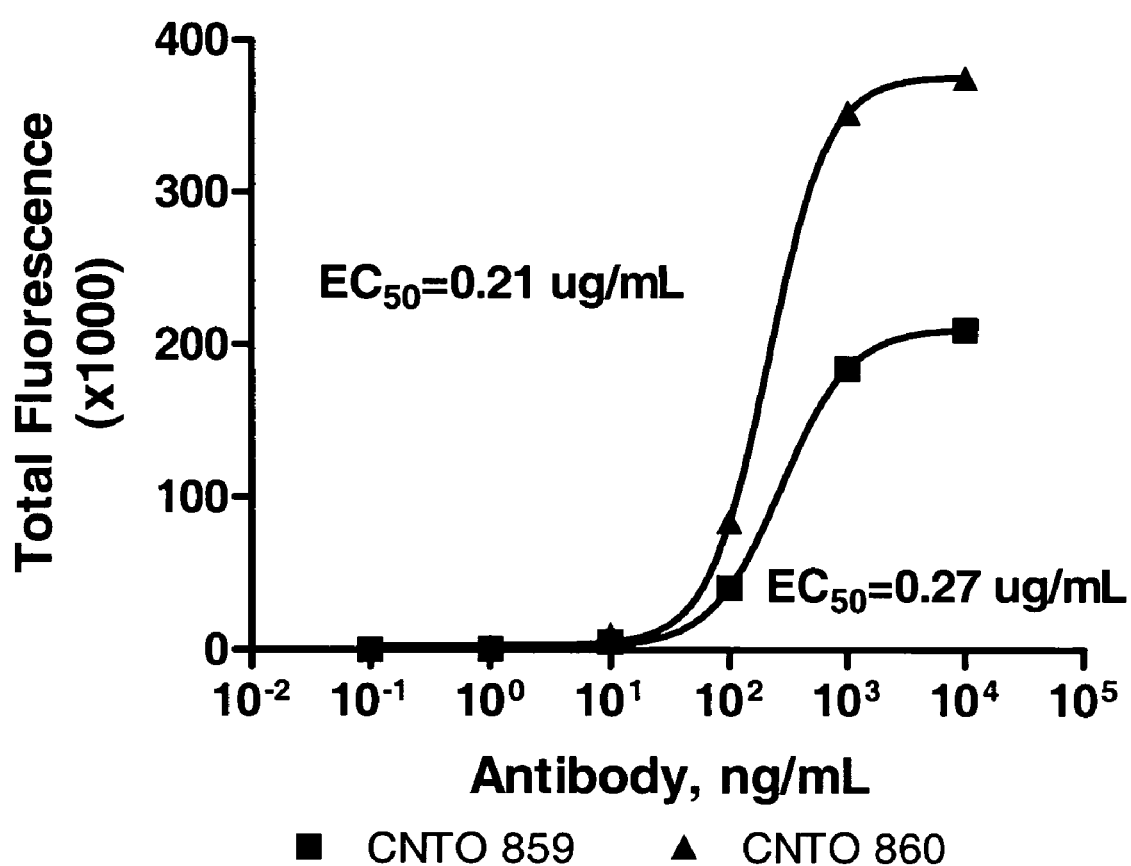
FIG. 12 is a graph showing the binding data for CNTO859 and CNTO860 to MDA-231 cells.
Figure 14:
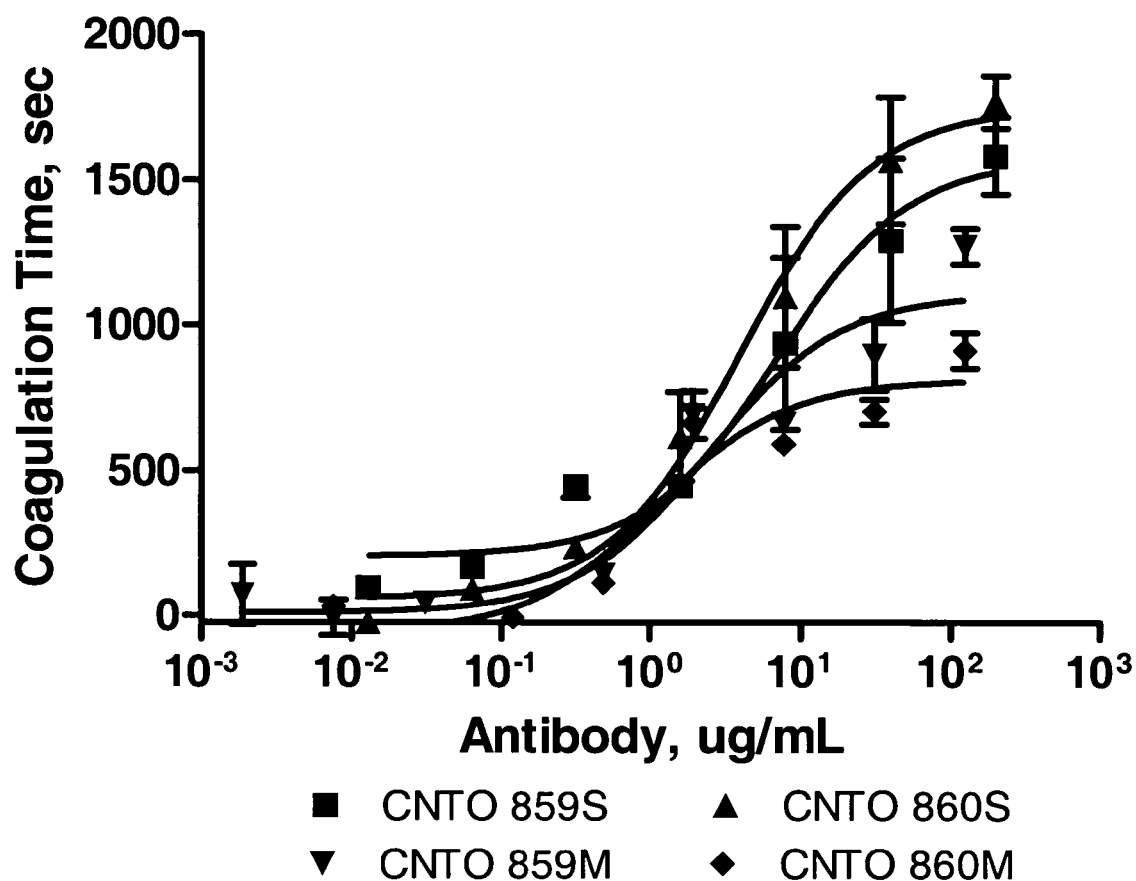
FIG. 14 is a graph showing the relationship between antibody concentration and prolongation of coagulation time.

CNTO 859 and CNTO 860 were shown to have identical binding and specificity. Both antibodies have equivalent affinity for TF on MDA-MB-231 human breast carcinoma cells as assessed by flow cytometry (FIG. 12). The differences in maximum fluorescence is attributed to differential recognition by a PE-labeled secondary. Both antibodies can inhibit FX activation to FXa with equal potency (FIG. 13). Both antibodies can block in vitro coagulation of human plasma in a prothrombin assay when both recombinant (S) and cell surface (M) expressed TF were used as the initiator (FIG. 14).

EXAMPLE 4

Isotype Switching to an IgG1 Conferred Enhanced ADCC Activity and FCR Binding

Effector functions contributing to enhanced tumor cell killing and removal were measured using in vitro assays.

Chromium Release ADCC Assay. 100 uL of freshly isolated PBMCs ($10^6$ cells), 50 uL of chromium-labeled MDA MB 231 target cells ($2 \times 10^4$) and 50 uL of 4× diluted antibodies/CM alone or 2% Triton X-100 were added to each well. A separate set of control samples did not include effector cells to account for any antibody-induced apoptosis effects. Samples were centrifuged briefly at 1000 rpm for 1 min to bring all the assay components in contact with each other. The cells were co-incubated with the added reagents for 4 hrs in a humifidied atmosphere at 37° C. and 5% $CO_2$ after which a 50 uL aliquot of the supernatant was transferred to a LumaPlate and assayed for radioactivity in a TopCount microplate scintillation counter (Packard).

Figure 15:
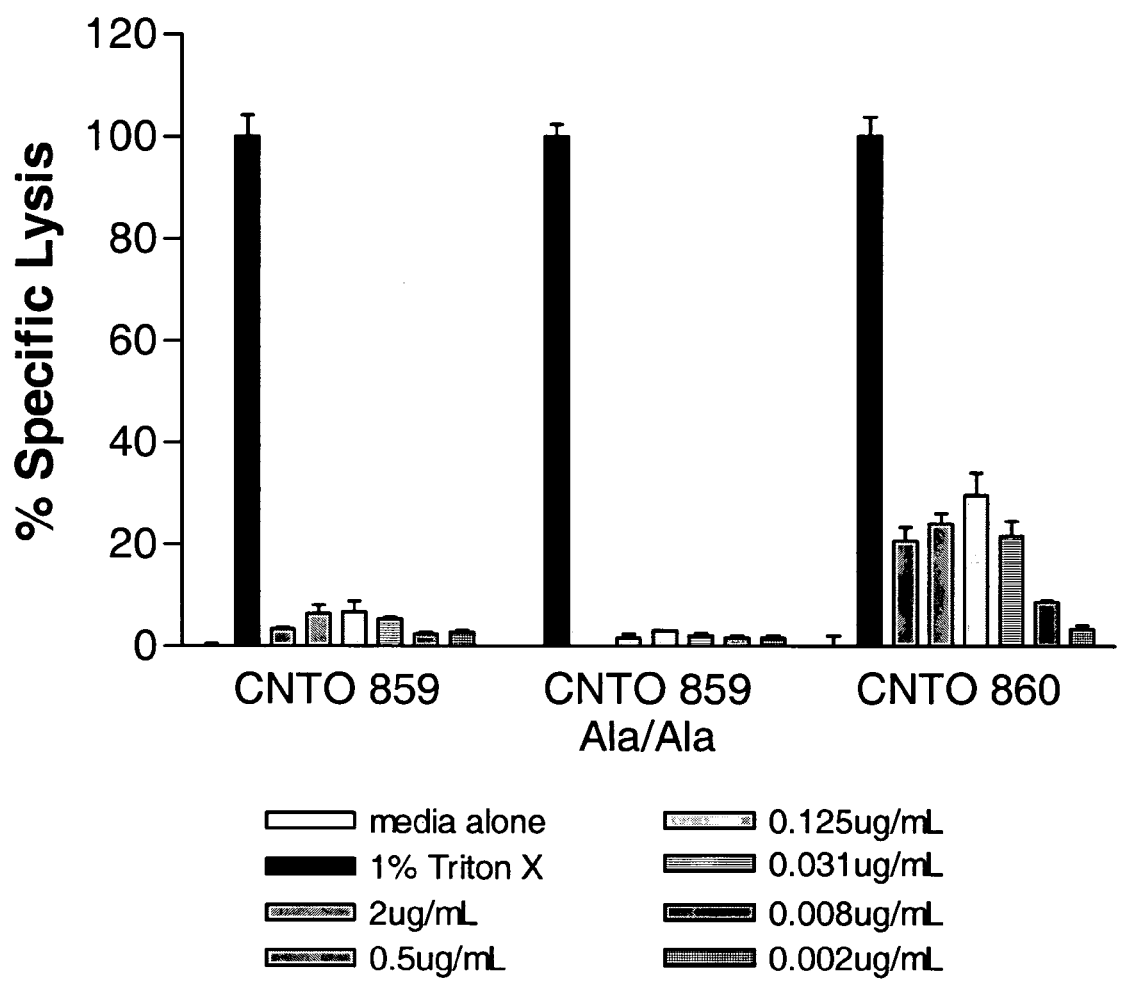
FIG. 15 is a bar graph showing the relative abilities of CNTO859, the CNTO859 with ala/ala mutations in the hinge region, and CNTO860 compared to non-specific and complete cell lysis by Triton-X.

Using chromium release as a measure of ADCC, CNTO 860 showed improved killing of MDA-MB-231 cells over CNTO 859 in a dose-dependent manner (FIG. 15). Error bars (SEM) were generated for triplicate samples.

Figure 16:
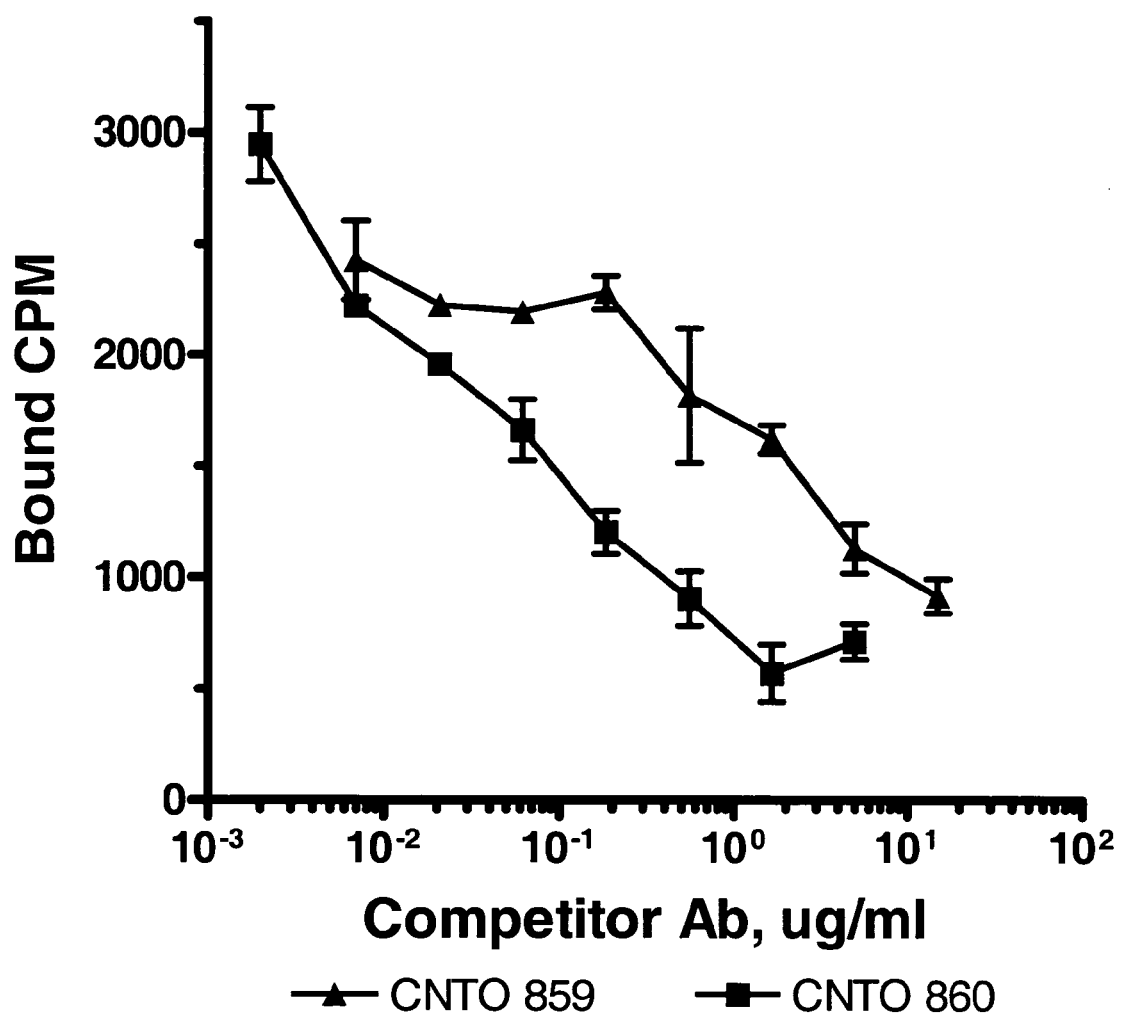
FIG. 16 is a graph showing the 10- to 100-fold enhancement of Fc receptor binding affinity of CNTO860 v CNTO859 in a competition assay using radiolabeled control antibody bound to U937 cells.

In a Fc receptor binding assay a radiolabeled control antibody was allowed to bind to U937 cells. Increasing amounts of CNTO 859 or CNTO 860 was added as competitors for binding to the FcR (FIG. 16). CNTO 860 is roughly 10-100× higher affinity for FcR binding than CNTO 859.

EXAMPLE 5

CNTO 860 is More potent in vivo in Inhibiting Tumor Growth, Delaying Tumor Onset and Reducing Tumor Incidence The primary purpose of this study is to investigate the differences, if any, of human antibody glycosylation and isotype in preventing tumor growth and neovascularization of an orthotopic MDA MB 231 human breast carcinoma xenograft in SCID Beige mice. In particular, we want to compare the efficacy of CNTO 860, an anti-human tissue factor IgG1 antibody to CNTO 859, our anti-tissue factor IgG4 antibody and their respective "Ala/Ala" mutants. Antibodies with ala/ala mutantions, as described above, are native human isotype and allotype heavy chain constant regions with alanine residues substituted for the native residues at aa residue positions 234 and 235.

Female SCID Beige mice (C.B-17/IcrCrl-scid-bgBR) approximately 18-20 g in weight were obtained from Charles River Laboratories and acclimated for 10-14 days prior to experimentation. For the study 48 mice were assigned to 6 groups, 8 animals per group. On day 0, $2.5 \times 10^6$ cells were implanted into the mammary fat pad (#2 or # right inguinal fat pad) of SCID/Beige mice in 50 uL PBS. Once-weekly therapy commenced 3 days post tumor cell implantation using either PBS, F105 isotype matched control antibody, CNTO 859, CNTO 860, CNTO 859 Ala/Ala or CNTO 860 Ala/Ala all at 0.1 mg/kg by i.v. injection. Animal weights and tumor volumes were monitored starting on day 3 and once weekly thereafter for 8 weeks. Tumor volumes were calculated as $(L \times W^2)/2$. Primary tumors were surgically removed, weighed and fixed in BZF solution. Samples were also retained for processing and IHC staining.

Figure 17:
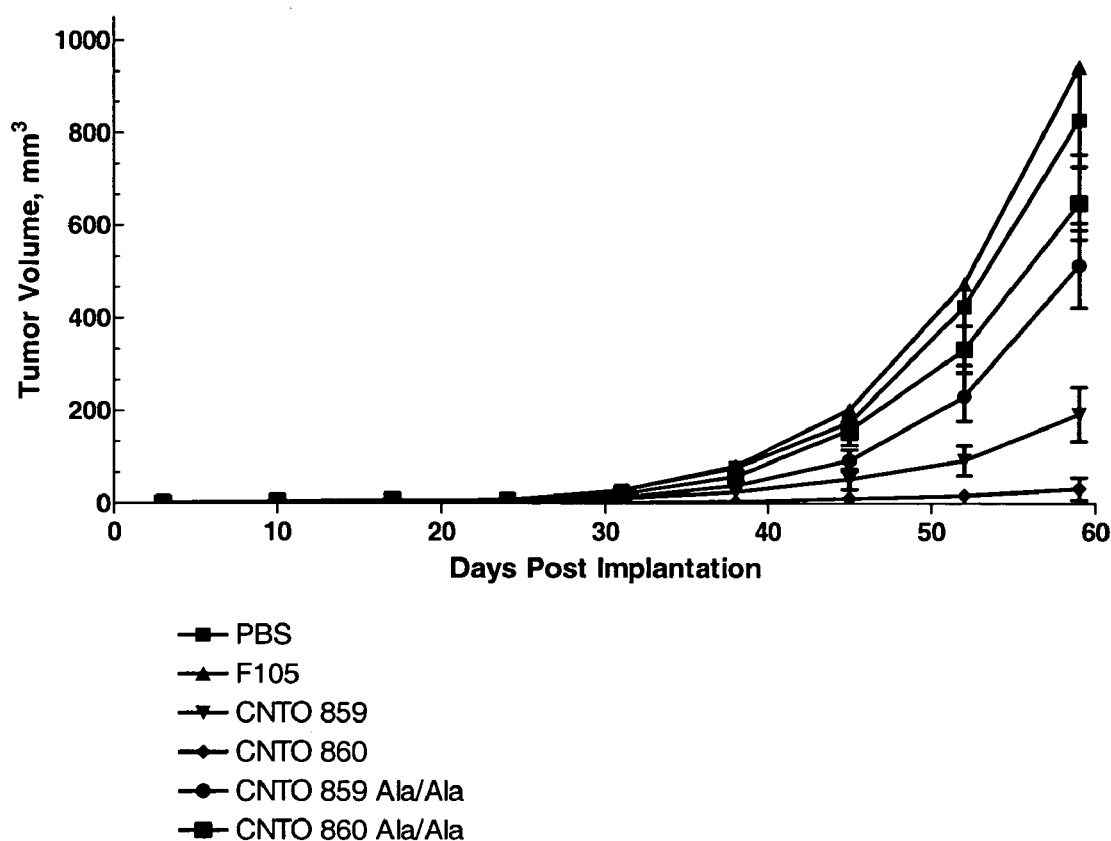
FIG. 17 is graph showing the mean tumor volume over time for mice bearing human breast tumor cells, MDA MB-231, implanted in the mammary fat pad and treated with 0.1 mg/kg of F105, CNTO 859, CNTO 860, CNTO 859 Ala/Ala and CNTO 860 Ala/Ala antibody or an equivalent volume of PBS.
Figure 18:
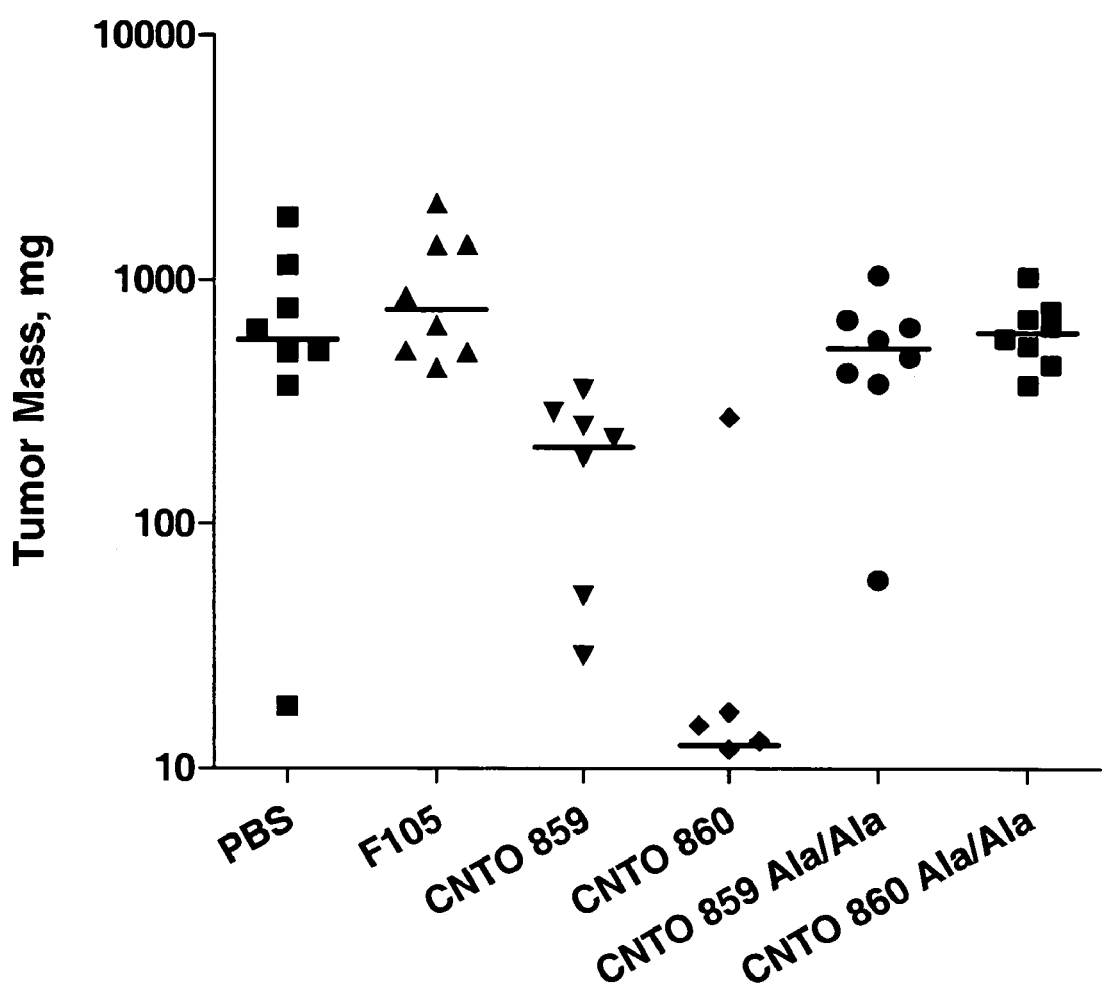
FIG. 18 is a scatter plot showing the final tumor weights for the mice as described for FIG. 17.
Figure 19:
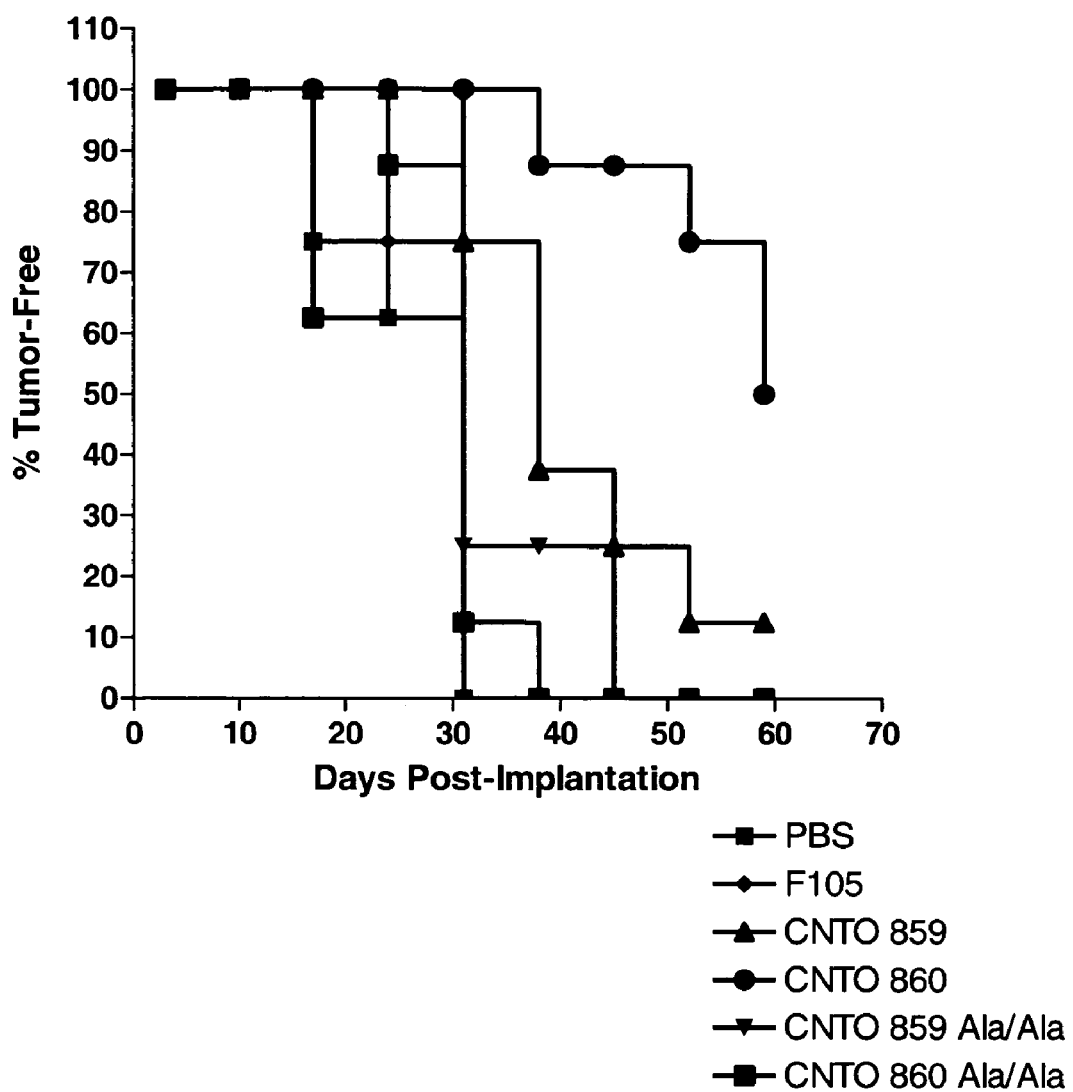
FIG. 19 is a graph showing the percent of mice (8 per group) with or without measurable sized tumors over the course of the experiment by treatment group as described for FIG. 17.

The results for this study, are shown graphically in FIGS. 17-19: mean tumor volume over time (FIG. 17), final tumor masses (FIG. 18) and tumor incidence results (FIG. 19). Using the dose of 0.1 mg/kg: CNTO 859 inhibited tumor growth by 75% (p<0.0478); CNTO 860 showed greater than 95% tumor inhibition (p<0.0001). Treatment groups receiving CNTO 859 Ala/Ala and CNTO 860 Ala/Ala antibodies showed a slight trend towards tumor inhibition, although statistical significance was not reached. CNTO 860 was also capable of delaying tumor onset by 21 days compared to control groups and protected 100% of the animals from developing tumors at day 31 (when all control treated animals harbored tumors), and by 50% at the end of the study (FIG. 19).

EXAMPLE 6

Contribution of Host Effector Function

Evaluation of anti-tissue factor combination therapy using CNTO 860 and the mouse surrogate antibody, PHD 126, in the orthotopic human breast carcinoma MDA MB 231 xenograft model in SCID Beige mice as described above. PHD 126 represents a anti-murine tissue factor surrogate of CNTO860 and is described in applicants co-pending application U.S. Ser. No. 60/565674. PHD 126 comprises a human anti-murine TF variable region fused to a murine IgG2a heavy chain constant region. Similar to human isotypes, murine antibodies have also been characterized for their ability to induce various effector functions such as ADCC, and complement mediated cytotoxicity. For example, murine macrophages are reportedly able to interact with mouse IgG2a antibodies to promote tumor cell killing. (Johnson et a. 1985. *Adv Exp Med Biol* 1985;184:75-80).

As PHD 126 recognizes murine tissue factor, it has the potential to react with the mouse vasculature and other murine components expressing TF (e.g. activated monocytes) whereas CNTO 860 will target the implanted human MDA MB 231 tumor cells.

The test antibodies are the humanized anti-human Tissue Factor antibody, CNTO 860 isotype IgG4 as described above and its isotype control antibody F105, and PDH 126 and its isotypic counterpart cVaM.

TABLE 5

| Group | Mice/Group | Antibody | Day 3 Initiation | Schedule (×8 weeks) |
|---|---|---|---|---|
| 1 | 6 | cVaM | 5 mg/kg | 2× week |
|   |   | F105 | 0.03 mg/kg | 1× week |
| 2 | 6 | PHD 126 | 5 mg/kg | 2× week |
|   |   | F105 | 0.03 mg/kg | 1× week |
| 3 | 6 | cVaM | 5 mg/kg | 2× week |
|   |   | CNTO 860 | 0.03 mg/kg | 1× week |
| 4 | 6 | PHD 126 | 5 mg/kg | 2× week |
|   |   | CNTO 860 | 0.03 mg/kg | 1× week |

Figure 20:
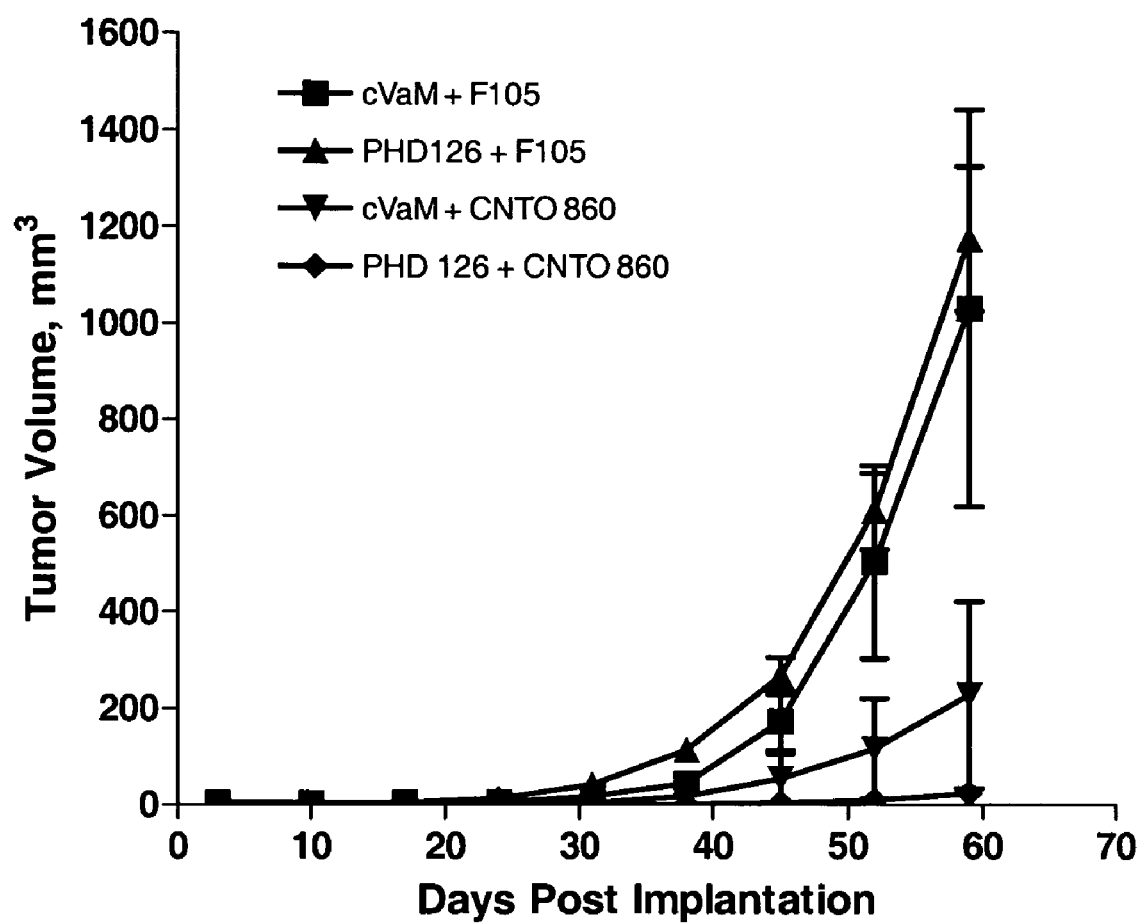
FIG. 20 is graph showing human breast tumor cell (MDA MB-231) growth over time in SCID beige mice treated with anti-human tissue factor (CNTO 860) plus an anti-mouse tissue factor (PHD 126) both of which of isotypes with capable of eliciting effector functions for the respective species. F105 and vCam are isotype matched control antibodies. Antibody injections were given once per week for 8 weeks.
Figure 21:
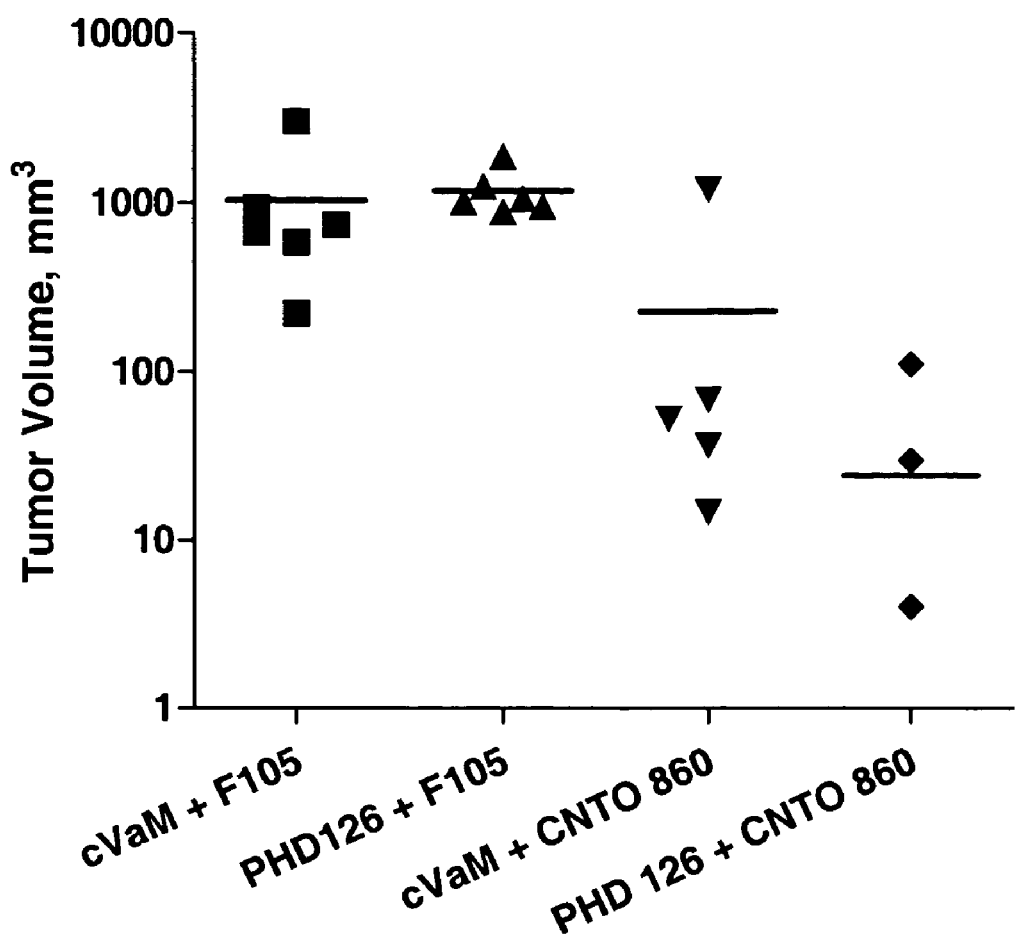
FIG. 21 is scatter plot of the individual final tumor masses for the experiment as described for FIG. 20.
Figure 22:
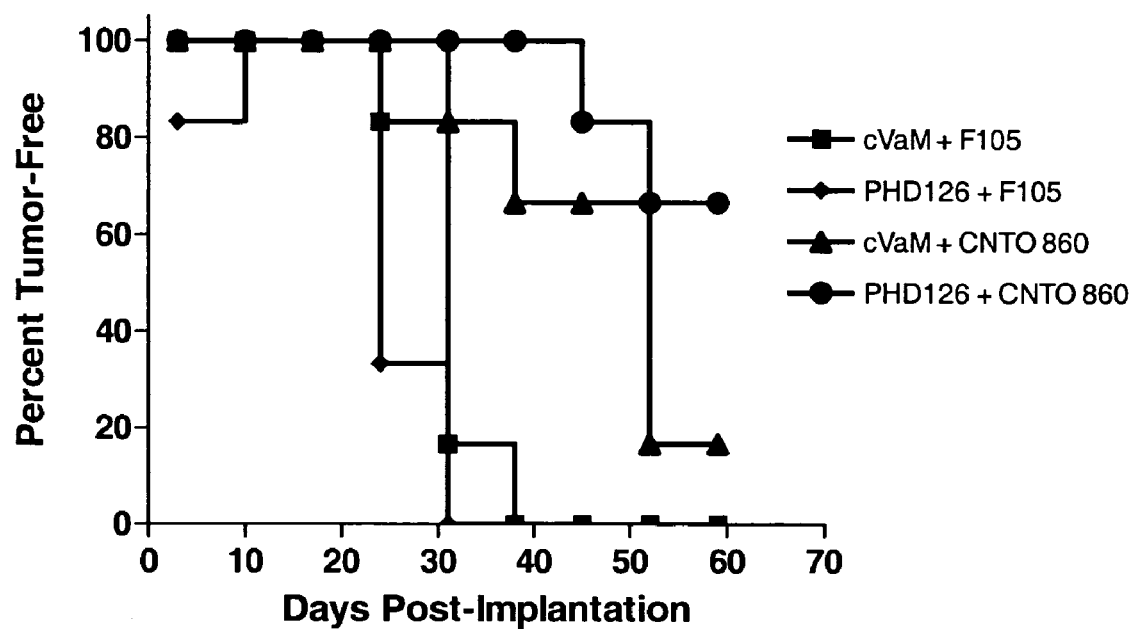
FIG. 22 is a plot of the percent of tumor free mice by group over time in the experiment as described for FIG. 20.

FIGS. 20-22 show the results of this experiment. CNTO 860, targeting only TF on the implanted tumor cells, was intentionally dosed at a partially effective dose of 0.03 mg/kg. FIG. 21 shows that treatment with this dose of CNTO 860 combined with the inactive control mouse IgG, cVaM, resulted in substantial but incomplete inhibition of tumor growth relative to the inactive cVaM+F105 control treatment group (77% reduction, p=0.0078, t-test). Treatment with PHD 126+F105, targeting only host TF on tumor stromal and endothelial cells, did not affect tumor inhibition in this model, as shown in FIG. 21.

The results of this study suggests that targeting TF only on tumor endothelial and stromal cells is insufficient to inhibit tumor growth in this model. However, combining CNTO 860 and PHD 126 in a regimen that targets both tumor cell TF and stromal TF results in improved tumor control relative to each therapy alone, as illustrated by the nearly complete suppression of tumor growth in FIG. 21. Combination therapy with CNTO 860+PHD 126 inhibited tumor growth by 97% compared to the control group (p=0.0039, t-test), by 90% relative to CNTO 860 monotherapy (p=0.0391) and by 98% versus PHD 126 monotherapy alone (p=0.0039, t-test). This interaction is, in fact, synergistic based on the observation that PHD 126 alone produced 0% inhibition but adds anti-tumor efficacy in combination. FIG. 21 shows the results of the experiment in the form of a scatter-plot of final tumor volumes and confirms the conclusions cited for FIG. 20.

FIG. 22 demonstrates that CNTO 860 therapy results in a delay of onset of measurable tumors but PHD 126 does not, consistent with the tumor volume data in FIGS. 20 and 21. The combination of CNTO 860 and PHD 126 results in a further delay of tumor onset and significantly reduces the incidence of tumor growth at the end of the study as compared to either agent alone. These results confirm the synergistic anti-tumor effects of targeting TF on both tumor cells and host stromal cells. Thus for the first time, it was demonstrated that targeting TF in the tumor stroma with a monoclonal antibody provides an anti-tumor benefit. Such stromal targeting is predicted with CNTO 860 in human cancer patients where all TF is of human origin and CNTO 860 will target both tumor cells and stromal cells simultaneously.

We claim:

1. An isolated antibody which binds tissue factor having the heavy chain amino acid sequence consisting of SEQ ID NO:2, and the light chain amino acid sequence consisting of SEQ ID NO:4.

2. The isolated antibody of claim 1, wherein the antibody binds to human tissue factor integrin subunit with a $K_D$ Of $10^{-9}$ M or less.

3. A composition comprising at least one isolated mammalian anti-tissue factor antibody according to claim 1, and at least ine pharmaceutically acceptable carrier or diluent.

4. A composition according to claim 3 wherein the antibody is combined with an anti-neoplastic agent selected from a radiopharmaceutical, an estrogen receptor modulator, a retinoid, a topoisomererase inhibitor, a cytotoxin, an alkylating agent, a nitrogen mustard, a nitrosourea, an antimetabolite, a mitotic inhibitor, and a radiosensitizer.

5. A composition according to claim 4 wherein the anti-neoplastic agent is dacarbazine.

6. An immunoconjugate comprising the antibody according to claim 1 linked to a therapeutic agent.

7. The immunoconjugate of claim 6 wherein the therapeutic agent is a cytotoxin.

8. The immunoconjugate of claim 6 wherein the therapeutic agent is a radioisotope.

9. A pharmaceutical composition comprising the immunoconjugate of any one of claims 6-8 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,605,235 B2 | Page 1 of 1 |
| APPLICATION NO. | : 11/010797 | |
| DATED | : October 20, 2009 | |
| INVENTOR(S) | : Anderson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 854 days.

Signed and Sealed this

Fifth Day of October, 2010

David J. Kappos
*Director of the United States Patent and Trademark Office*